(12) United States Patent
Fischer et al.

(10) Patent No.: US 7,153,931 B1
(45) Date of Patent: *Dec. 26, 2006

(54) TRANSPORT VECTORS

(75) Inventors: Peter M. Fischer, Angus (GB); Nikolai Zhelev, Newport-on-tay (GB); Shudong Wang, Forfar (GB)

(73) Assignee: Cyclacel Limited, Dundee (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/438,460

(22) Filed: Nov. 12, 1999

(30) Foreign Application Priority Data

| Nov. 13, 1998 | (GB) | ................................................ 9825000 |
| Nov. 13, 1998 | (GB) | ................................................ 9825001 |
| Feb. 4, 1999 | (GB) | ................................................ 9902522 |
| Feb. 4, 1999 | (GB) | ................................................ 9902525 |
| Jun. 22, 1999 | (GB) | ................................................ 9914578 |

(51) Int. Cl.
C07K 7/02 (2006.01)
C07K 7/06 (2006.01)
C07K 7/08 (2006.01)

(52) U.S. Cl. .................... 530/326; 530/327; 530/328; 530/329; 530/323; 530/402

(58) Field of Classification Search ......... 530/323–329, 530/402; 514/13–17
See application file for complete search history.

(56) References Cited

U.S. PATENT DOCUMENTS

| 4,847,240 A | 7/1989 | Ryser et al. |
| 5,043,329 A | 8/1991 | Lichtenberger |
| 5,179,086 A | 1/1993 | Flender |
| 5,580,563 A | 12/1996 | Tam |
| 5,888,762 A | 3/1999 | Joliot et al. |
| 6,025,140 A | 2/2000 | Langel et al. |
| 6,080,724 A | 6/2000 | Chassaing et al. |
| 6,472,507 B1 | 10/2002 | Fischer et al. |

FOREIGN PATENT DOCUMENTS

| EP | 0751225 A1 | 10/1991 |
| EP | 0485578 | 10/1996 |
| EP | 751225 * | 1/1997 |
| GB | 2 340 121 | 2/2000 |
| WO | WO 91/18981 A2 | 12/1991 |
| WO | WO 95/33766 | 12/1995 |
| WO | WO 95/34295 | 12/1995 |
| WO | WO 97/12912 | 4/1997 |
| WO | WO 97/19954 A1 | 6/1997 |
| WO | WO 97/25070 | 7/1997 |
| WO | WO 98/13059 A1 | 4/1998 |
| WO | WO 98/38861 | 9/1998 |
| WO | WO 98/56938 | 12/1998 |
| WO | WO 99/05302 A1 | 2/1999 |
| WO | WO 99/11809 | 3/1999 |
| WO | WO 00/01417 | 1/2000 |

OTHER PUBLICATIONS

Caplus Database Accession No. 165206, 1997.*
Fischer et al (Journal of Peptide Research, 2000, vol. 55, pp. 163–172).*
U.S. Appl. No. 10/210,660, Fischer et al.
Brugidou, J. et al. (1995) "The Retro–Inverso Form Of A Homeobox–Derived Short Peptide Is Rapidly Internalised By Cultured Neurones: A New Basis For An Efficient Intracellular Delivery System" Biochemical and Biophysical Research Communications, vol. 214, No. 2, pp. 685–693.
Derossi, Daniele et al. (1994) "The Third Helix of the Antennapedia Homeodomain Translocates Through Biological Membranes" The Journal of Biological Chemistry, vol. 269, No. 14, pp. 10444–10450.
Derossi, Daniele et al (1996) "Cell Internalization of the Third Helix of the Antennapedia Homeodomain Is Receptor–Independent" The Journal of Biological Chemistry, vol. 271, No. 30, pp. 18188–18193.
Plank, Christian (1999) "Branched Cationic Peptides For Gene Delivery: Role of Type and Number of Cationic Residues In Formation And In Vitro Activity of DNA Polyplexes" Human Gene Therapy, vol. 10, pp. 319–332.
Prochiantz, Alain (1996) "Getting Hydrophilic Compounds Into Cells: Lessons From Homeopeptides" Current Opinion in Neurobiology, vol. 6 , pp. 629–634.
Simmons, Carla G. (1997) "Synthesis And Membrane Permeability of PNA–Peptide Conjugates", Bioorganic & Medicinal Chemistry Letters, vol. 7, No. 23, pp. 3001–3006.
Schutze–Redelmeier, Marie–Paule et al. (1996) "Introduction of Exogenous Antigens Into The MHC Class I Processing And Presentation Pathway By Drosophila Antennapedia Homeodomain Primes Cytotoxic T Cells In Vivo" The Journal of Immunologists, pp. 651–655.
Derossi D, et al. "Trojan peptides: the penetratin system for intracellular delivery." *Trends Cell Biol.* Feb. 1998;8(2):84–7.
Fischer PM, et al. "Structure–activity relationship of truncated and substituted analogues of the intracellular delivery vector Penetratin". *J Pept Res.* Feb. 2000;55(2):163–72.

* cited by examiner

*Primary Examiner*—Karen A. Canella
(74) *Attorney, Agent, or Firm*—Lahive & Cockfield, LLP; Giulio A. DeConti, Jr.; Cynthia L. Kanik

(57) ABSTRACT

The invention relates to modified and truncated forms of the membrane transport vector penetratin. Such truncated forms include 7-mer peptides that may in themselves include further variation.

93 Claims, 5 Drawing Sheets

SEQUENCE LISTING

<160> NUMBER OF SEQ ID NOS: 66

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
 1               5                  10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence
<221> NAME/KEY: MOD_RES
<222> LOCATION: (7)
<223> OTHER INFORMATION: AMIDATION; the carboxy terminal lysine residue
      may have its carboxyl group converted into an carboxamide group.

<400> SEQUENCE: 2

Arg Arg Met Lys Trp Lys Lys
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 3

Arg Arg Met Trp Lys Lys Lys
 1               5

<210> SEQ ID NO 4
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Xaa is norleucine ornithine
<223> OTHER INFORMATION: Description of Artificial Sequence: Synthetic
      sequence

<400> SEQUENCE: 4

Arg Arg Xaa Lys Trp Lys Lys
 1               5

<210> SEQ ID NO 5
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Xaa is norleucine ornithine
<223> OTHER INFORMATION: Description of Artificial Sequence: Synthetic
      sequence

<400> SEQUENCE: 5

Arg Arg Xaa Trp Lys Lys Lys

```
<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 6

Asn Arg Arg Met Lys Trp Lys Lys
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 7

Gln Asn Arg Arg Met Lys Trp Lys Lys
  1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 8

Phe Gln Asn Arg Arg Met Lys Trp Lys Lys
  1               5                  10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 9

Lys Arg Met Lys Trp Lys Lys
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 10

Arg Lys Met Lys Trp Lys Lys
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
                    sequence

<400> SEQUENCE: 11

Arg Arg Glu Lys Trp Lys Lys
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 12

Arg Arg Gln Lys Trp Lys Lys
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 13

Arg Arg Met Lys Gln Lys Lys
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 14

Arg Arg Met Lys Trp Phe Lys
 1               5

<210> SEQ ID NO 15
<211> LENGTH: 7
<212> TYPE: PRT
<213> ORGANISM: Artificial Sequence
<220> FEATURE:
<221> NAME/KEY: MOD_RES
<222> LOCATION: (2)
<223> OTHER INFORMATION: Xaa is norleucine ornithine
<223> OTHER INFORMATION: Description of Artificial Sequence: Synthetic
      sequence

<400> SEQUENCE: 15

Arg Xaa Arg Lys Trp Lys Lys
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 16

Arg Arg Met Trp Lys Lys Lys
 1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 17

Arg Arg Met Lys Lys Trp Lys
 1               5

<210> SEQ ID NO 18
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Xaa is norleucine ornithine
<223> OTHER INFORMATION: Description of Artificial Sequence: Synthetic
      sequence

<400> SEQUENCE: 18

Arg Arg Xaa Lys Lys Trp Lys
 1               5

<210> SEQ ID NO 19
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 19

Ala Arg Gln Ile Lys Ile Trp Phe Gln Asn Arg Arg Met Lys Trp Lys
 1               5                  10                  15

Lys

<210> SEQ ID NO 20
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 20

Ala Ala Gln Ile Lys Ile Trp Phe Gln Asn Arg Arg Met Lys Trp Lys
 1               5                  10                  15

Lys

<210> SEQ ID NO 21
<211> LENGTH: 17
```

```
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 21

Ala Arg Ala Ile Lys Ile Trp Phe Gln Asn Arg Arg Met Lys Trp Lys
 1               5                  10                  15

Lys

<210> SEQ ID NO 22
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 22

Ala Arg Gln Ala Lys Ile Trp Phe Gln Asn Arg Arg Met Lys Trp Lys
 1               5                  10                  15

Lys

<210> SEQ ID NO 23
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 23

Ala Arg Gln Ile Ala Ile Trp Phe Gln Asn Arg Arg Met Lys Trp Lys
 1               5                  10                  15

Lys

<210> SEQ ID NO 24
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 24
```

```
Ala Arg Gln Ile Lys Ala Trp Phe Gln Asn Arg Arg Met Lys Trp Lys
 1               5                  10                  15

Lys

<210> SEQ ID NO 25
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 25

Ala Arg Gln Ile Lys Ile Ala Phe Gln Asn Arg Arg Met Lys Trp Lys
 1               5                  10                  15

Lys

<210> SEQ ID NO 26
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 26

Ala Arg Gln Ile Lys Ile Trp Ala Gln Asn Arg Arg Met Lys Trp Lys
 1               5                  10                  15

Lys

<210> SEQ ID NO 27
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 27

Ala Arg Gln Ile Lys Ile Trp Phe Ala Asn Arg Arg Met Lys Trp Lys
 1               5                  10                  15

Lys

<210> SEQ ID NO 28
<211> LENGTH: 17
<212> TYPE: PRT
<213> ORGANISM: Artificial Sequence
<220> FEATURE:
<221> NAME/KEY: MOD_RES
```

```
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 28

Ala Arg Gln Ile Lys Ile Trp Phe Gln Ala Arg Arg Met Lys Trp Lys
 1               5                  10                  15

Lys

<210> SEQ ID NO 29
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 29

Ala Arg Gln Ile Lys Ile Trp Phe Gln Asn Ala Arg Met Lys Trp Lys
 1               5                  10                  15

Lys

<210> SEQ ID NO 30
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 30

Ala Arg Gln Ile Lys Ile Trp Phe Gln Asn Arg Ala Met Lys Trp Lys
 1               5                  10                  15

Lys

<210> SEQ ID NO 31
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 31

Ala Arg Gln Ile Lys Ile Trp Phe Gln Asn Arg Arg Ala Lys Trp Lys
 1               5                  10                  15
```

Lys

<210> SEQ ID NO 32
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 32

Ala Arg Gln Ile Lys Ile Trp Phe Gln Asn Arg Arg Met Ala Trp Lys
 1               5                  10                  15

Lys

<210> SEQ ID NO 33
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 33

Ala Arg Gln Ile Lys Ile Trp Phe Gln Asn Arg Arg Met Lys Ala Lys
 1               5                  10                  15

Lys

<210> SEQ ID NO 34
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)
<223> OTHER INFORMATION: AMIDATION
<223> OTHER INFORMATION: Description of Artificial Sequence: Synthetic
      sequence

<400> SEQUENCE: 34

Ala Arg Gln Ile Lys Ile Trp Phe Gln Asn Arg Arg Met Lys Trp Ala
 1               5                  10                  15

Lys

<210> SEQ ID NO 35
<211> LENGTH: 17
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (17)

```
<223> OTHER INFORMATION: AMIDATION
<223> OTHER INFORMATION: Description of Artificial Sequence: Synthetic
      sequence

<400> SEQUENCE: 35

Ala Arg Gln Ile Lys Ile Trp Phe Gln Asn Arg Arg Met Lys Trp Lys
 1               5                  10                  15

Ala

<210> SEQ ID NO 36
<211> LENGTH: 7
<212> TYPE: PRT
<213> ORGANISM: Artificial Sequence
<220> FEATURE:
<221> NAME/KEY: MOD_RES
<222> LOCATION: (5)
<223> OTHER INFORMATION: Xaa is norleucine ornithine
<223> OTHER INFORMATION: Description of Artificial Sequence: Synthetic
      sequence

<400> SEQUENCE: 36

Lys Lys Trp Lys Xaa Arg Arg
 1               5

<210> SEQ ID NO 37
<211> LENGTH: 16
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (16)
<223> OTHER INFORMATION: AMIDATION
<223> OTHER INFORMATION: Description of Artificial Sequence: Synthetic
      sequence

<400> SEQUENCE: 37

Ala Arg Gln Ile Lys Ile Trp Phe Gln Asn Arg Arg Met Lys Trp Lys
 1               5                  10                  15

<210> SEQ ID NO 38
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (15)
<223> OTHER INFORMATION: AMIDATION
<223> OTHER INFORMATION: Description of Artificial Sequence: Synthetic
      sequence

<400> SEQUENCE: 38

Ala Arg Gln Ile Lys Ile Trp Phe Gln Asn Arg Arg Met Lys Trp
 1               5                  10                  15

<210> SEQ ID NO 39
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (14)
```

```
<223> OTHER INFORMATION: AMIDATION
<223> OTHER INFORMATION: Description of Artificial Sequence: Synthetic
      sequence

<400> SEQUENCE: 39

Ala Arg Gln Ile Lys Ile Trp Phe Gln Asn Arg Arg Met Lys
 1               5                  10

<210> SEQ ID NO 40
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (13)
<223> OTHER INFORMATION: AMIDATION
<223> OTHER INFORMATION: Description of Artificial Sequence: Synthetic
      sequence

<400> SEQUENCE: 40

Ala Arg Gln Ile Lys Ile Trp Phe Gln Asn Arg Arg Met
 1               5                  10

<210> SEQ ID NO 41
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (12)
<223> OTHER INFORMATION: AMIDATION
<223> OTHER INFORMATION: Description of Artificial Sequence: Synthetic
      sequence

<400> SEQUENCE: 41

Ala Arg Gln Ile Lys Ile Trp Phe Gln Asn Arg Arg
 1               5                  10

<210> SEQ ID NO 42
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (11)
<223> OTHER INFORMATION: AMIDATION
<223> OTHER INFORMATION: Description of Artificial Sequence: Synthetic
      sequence

<400> SEQUENCE: 42

Ala Arg Gln Ile Lys Ile Trp Phe Gln Asn Arg
 1               5                  10

<210> SEQ ID NO 43
<211> LENGTH: 10
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
```

```
<222> LOCATION: (10)
<223> OTHER INFORMATION: AMIDATION
<223> OTHER INFORMATION: Description of Artificial Sequence: Synthetic
      sequence

<400> SEQUENCE: 43

Ala Arg Gln Ile Lys Ile Trp Phe Gln Asn
 1               5                  10

<210> SEQ ID NO 44
<211> LENGTH: 9
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (9)
<223> OTHER INFORMATION: AMIDATION
<223> OTHER INFORMATION: Description of Artificial Sequence: Synthetic
      sequence

<400> SEQUENCE: 44

Ala Arg Gln Ile Lys Ile Trp Phe Gln
 1               5

<210> SEQ ID NO 45
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (7)
<223> OTHER INFORMATION: AMIDATION
<223> OTHER INFORMATION: Description of Artificial Sequence: Synthetic
      sequence

<400> SEQUENCE: 45

Ala Arg Gln Ile Lys Ile Trp
 1               5

<210> SEQ ID NO 46
<211> LENGTH: 16
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (16)
<223> OTHER INFORMATION: AMIDATION
<223> OTHER INFORMATION: Description of Artificial Sequence: Synthetic
      sequence

<400> SEQUENCE: 46

Ala Gln Ile Lys Ile Trp Phe Gln Asn Arg Arg Met Lys Trp Lys Lys
 1               5                  10                  15

<210> SEQ ID NO 47
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
```

```
<221> NAME/KEY: MOD_RES
<222> LOCATION: (15)
<223> OTHER INFORMATION: AMIDATION
<223> OTHER INFORMATION: Description of Artificial Sequence: Synthetic
      sequence

<400> SEQUENCE: 47

Ala Ile Lys Ile Trp Phe Gln Asn Arg Arg Met Lys Trp Lys Lys
 1               5                  10                  15

<210> SEQ ID NO 48
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (14)
<223> OTHER INFORMATION: AMIDATION
<223> OTHER INFORMATION: Description of Artificial Sequence: Synthetic
      sequence

<400> SEQUENCE: 48

Ala Lys Ile Trp Phe Gln Asn Arg Arg Met Lys Trp Lys Lys
 1               5                  10

<210> SEQ ID NO 49
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (13)
<223> OTHER INFORMATION: AMIDATION
<223> OTHER INFORMATION: Description of Artificial Sequence: Synthetic
      sequence

<400> SEQUENCE: 49

Ala Ile Trp Phe Gln Asn Arg Arg Met Lys Trp Lys Lys
 1               5                  10

<210> SEQ ID NO 50
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (12)
<223> OTHER INFORMATION: AMIDATION
<223> OTHER INFORMATION: Description of Artificial Sequence: Synthetic
      sequence

<400> SEQUENCE: 50

Ala Trp Phe Gln Asn Arg Arg Met Lys Trp Lys Lys
 1               5                  10

<210> SEQ ID NO 51
<211> LENGTH: 11
<212> TYPE: PRT
<213> ORGANISM: Artificial Sequence
<220> FEATURE:
<221> NAME/KEY: MOD_RES
<222> LOCATION: (1)
```

```
<223> OTHER INFORMATION: bAla
<221> NAME/KEY: MOD_RES
<222> LOCATION: (11)
<223> OTHER INFORMATION: AMIDATION
<223> OTHER INFORMATION: Description of Artificial Sequence: Synthetic
      sequence

<400> SEQUENCE: 51

Ala Phe Gln Asn Arg Arg Met Lys Trp Lys Lys
 1               5                  10

<210> SEQ ID NO 52
<211> LENGTH: 10
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (10)
<223> OTHER INFORMATION: AMIDATION
<223> OTHER INFORMATION: Description of Artificial Sequence: Synthetic
      sequence

<400> SEQUENCE: 52

Ala Gln Asn Arg Arg Met Lys Trp Lys Lys
 1               5                  10

<210> SEQ ID NO 53
<211> LENGTH: 9
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (9)
<223> OTHER INFORMATION: AMIDATION
<223> OTHER INFORMATION: Description of Artificial Sequence: Synthetic
      sequence

<400> SEQUENCE: 53

Ala Asn Arg Arg Met Lys Trp Lys Lys
 1               5

<210> SEQ ID NO 54
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: bAla
<221> NAME/KEY: MOD_RES
<222> LOCATION: (8)
<223> OTHER INFORMATION: AMIDATION
<223> OTHER INFORMATION: Description of Artificial Sequence: Synthetic
      sequence

<400> SEQUENCE: 54

Ala Arg Arg Met Lys Trp Lys Lys
 1               5

<210> SEQ ID NO 55
<211> LENGTH: 7
<212> TYPE: PRT
<213> ORGANISM: Artificial Sequence
<220> FEATURE:
<221> NAME/KEY: MOD_RES
```

```
<222> LOCATION: (1)
<223> OTHER INFORMATION: bAla
<221> NAME/KEY: MOD_RES
<222> LOCATION: (7)
<223> OTHER INFORMATION: AMIDATION
<223> OTHER INFORMATION: Description of Artificial Sequence: Synthetic
      sequence

<400> SEQUENCE: 55

Ala Arg Met Lys Trp Lys Lys
 1               5

<210> SEQ ID NO 56
<211> LENGTH: 16
<212> TYPE: PRT
<213> ORGANISM: Artificial Sequence
<220> FEATURE:
<221> NAME/KEY: MOD_RES
<222> LOCATION: (12)
<223> OTHER INFORMATION: Xaa is norleucine ornithine
<223> OTHER INFORMATION: Description of Artificial Sequence: Synthetic
      sequence

<400> SEQUENCE: 56

Arg Gln Ile Lys Ile Trp Phe Gln Asn Arg Arg Xaa Lys Trp Lys Lys
 1               5                  10                  15

<210> SEQ ID NO 57
<211> LENGTH: 16
<212> TYPE: PRT
<213> ORGANISM: Artificial Sequence
<220> FEATURE:
<221> NAME/KEY: MOD_RES
<222> LOCATION: (5)
<223> OTHER INFORMATION: Xaa is norleucine ornithine
<223> OTHER INFORMATION: Description of Artificial Sequence: Synthetic
      sequence

<400> SEQUENCE: 57

Lys Lys Trp Lys Xaa Arg Arg Asn Gln Phe Trp Ile Lys Ile Gln Arg
 1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 58

Arg Gln Ile Lys Ile Trp Phe Pro Asn Arg Arg Met Lys Trp Lys Lys
 1               5                  10                  15

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 59

Arg Gln Pro Ile Lys Ile Trp Phe Pro Asn Arg Arg Met Pro Trp Lys
 1               5                  10                  15

Lys

<210> SEQ ID NO 60
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 60

Arg Gln Ile Lys Ile Phe Phe Gln Asn Arg Arg Met Lys Phe Lys Lys
 1               5                  10                  15

<210> SEQ ID NO 61
<211> LENGTH: 9
<212> TYPE: PRT
<213> ORGANISM: Artificial Sequence
<220> FEATURE:
<221> NAME/KEY: MOD_RES
<222> LOCATION: (2)
<223> OTHER INFORMATION: bAla
<221> NAME/KEY: MOD_RES
<222> LOCATION: (9)
<223> OTHER INFORMATION: AMIDATION
<223> OTHER INFORMATION: Description of Artificial Sequence: Synthetic
      sequence

<400> SEQUENCE: 61

Cys Ala Arg Arg Met Lys Trp Lys Lys
 1               5

<210> SEQ ID NO 62
<211> LENGTH: 9
<212> TYPE: PRT
<213> ORGANISM: Artificial Sequence
<220> FEATURE:
<221> NAME/KEY: MOD_RES
<222> LOCATION: (9)
<223> OTHER INFORMATION: AMIDATION
<223> OTHER INFORMATION: Description of Artificial Sequence: Synthetic
      sequence

<400> SEQUENCE: 62

Cys Arg Arg Met Lys Trp Lys Lys Cys
 1               5

<210> SEQ ID NO 63
<211> LENGTH: 20
<212> TYPE: PRT
<213> ORGANISM: Artificial Sequence
<220> FEATURE:
<221> NAME/KEY: MOD_RES
<222> LOCATION: (20)
<223> OTHER INFORMATION: AMIDATION
<223> OTHER INFORMATION: Description of Artificial Sequence: Synthetic
      sequence

<400> SEQUENCE: 63

Cys Arg Gln Ile Lys Ile Trp Phe Gln Asn Arg Arg Met Lys Trp Lys
 1               5                  10                  15

Lys Gly Cys Gly
            20

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Penetratin
      variant

<400> SEQUENCE: 64
```

```
Lys Trp Lys Lys Lys Trp Lys Lys Lys Trp Lys Lys Lys Trp Lys Lys
1               5               10              15

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 65

Lys Trp Lys Lys Lys Trp Lys Lys Lys Gly Gly Cys
1               5               10

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 66

Lys Trp Lys Lys
1
```

TRANSPORT VECTORS

RELATED APPLICATIONS

This application claims priority to the following Great Britain applications: GB9825000.4, GB9825001.2 (filed on 13 Nov. 1998), GB 9902525.6, GB 9902522.3 (filed on 4 Feb. 1999, and GB 9914578.1 (filed on 22 Jun. 1999), the contents of which are hereby incorporated by reference.

BACKGROUND

The present invention relates to novel membrane translocation peptide carrier moieties and membrane translocation vectors comprising a novel peptide carrier moiety together with a cargo moiety, of use in the improved delivery of therapeutic agents into target cells.

The pharmaceutical industry has for many years concerned itself with the efficient delivery of therapeutic agents. This problem may be attributed to the short clearance time of the agent in the body (short half-life), the location of the site of action or possibly the nature of the therapeutic agent itself, for example, its solubility, hydrophobicity etc. Thus, many developments and strategies have been adopted, including formulating the therapeutic agent so as to protect it from a hostile environment on route to its site of action, by for example, enterically coated tablets, controlled release devices and the like.

The development of peptide derived therapeutic agents has posed a further problem due their susceptibility to enzymatic degradation not only in the GI tract but also in the bloodstream. An example of how this problem has been addressed relates to the incorporation of the peptides into liposomes or polymeric microspheres that target the peptides to the lymph system.

A further related problem, especially for therapeutic agents that function intracellularly is the barrier posed by the cell membrane. Thus, it may be possible to increase the half life of the agent or ensure that it passes through the body without being degraded, but many agents must actually enter cells to exert their therapeutic effect.

Homeoproteins are trans-activating factors involved in multiple morphological processes. They bind to DNA through a sequence of 60 amino acid residues, the so-called homeodomain. The structure of this domain consists of three α-helices, interrupted by a β-turn between helices 2 and 3 (Gehring, W. J. et al., (1990) Trends Genet 6, 323–9). The phylogenetic relationship between numerous homeoproteins is striking at the level of the homeodomain and particularly within the third α-helix. This helix is responsible for both the interaction with DNA, as well as the capacity of homeoproteins to translocate across cell membranes to cell nuclei in a non-specific manner.

European Patent 485578 discloses that the homeodomain and specifically, helix 3 of a homeobox peptide, particularly that derived from the Drosophila Antennapedia, is of use as an intracellular transport vector. The patent disclosed that a specific 57 amino acid sequence of a Drosophila Antennapedia homeopeptide (referred to as the pAntp peptide) was capable of penetrating fibroblasts and embryo cells (in vivo). Emphasis was placed upon the last 27 amino acids of the sequence that correspond with the helix 3 and 4. There is no description of the pAntp peptide being linked to any other peptide or therapeutic agent.

Subsequent disclosures (Derossi D et al., J Biol Chem (1994) 269, 10444–10450, Derossi D et al., J Biol Chem (1996) 271, 18188–18193, Joliot A H et al., (1991) The New Biol 3, 1121–1134 and PNAS (1991) 88, 1864–1868, Perez F et al., J Cell Sci (1992) 102, 712–722), have focused on a 16 amino acid synthetic peptide derived from the third helix of the Antennapedia homeodomain that may be used for the intracellular delivery of bioactive products and antisense oligonucleotides. The amino acid sequence of this peptide is RQIKIWFQNRRMKWKK (SEQ ID No. 1) also known as penetratin. In the course of their investigations the above authors synthesized several variants on this sequence, these corresponding to residues 41–60, 41–55 and 46–60 of the pAntp peptide and showed that in all cases, the only peptides to internalise into the cells were those that included the residues 43–58 (Derossi D et al., supra.).

In an effort to prevent the enzymatic cleavage of this peptide Brugidou J et al., (Biochem Biophys Res Comm (1995) 214(2), 685–693) prepared a retro-inverso form (D amino acids in reverse order) of SEQ ID No. 1, substituting the two isoleucine resides at positions 3 and 5 of penetratin with valine and adding a glycine residue at the C-terminus to facilitate binding to a resin. A further retro-inverso form was prepared replacing the extra glycine with a cholesterol moiety attached via a sulfhydryl linker group. The addition of the cholesterol moiety improved penetration due to the increased hydrophobicity of the molecule.

This development of the retro-inverso form of penetratin has given rise to WO 97/12912 that discloses peptides of 16 amino acids comprising between 6 and 10 hydrophobic amino acids wherein the sixth amino acid from either end must be tryptophan. This disclosure attempts to define the minimal characteristics of sequences capable of acting as internalisation vectors as being the retention of a tryptophan residue at the sixth position from the amino terminus and that the peptide contains from 6 to 10 hydrophobic amino acid residues (the classification of hydrophobic amino residues in WO97/12912 is not believed to be in agreement with the generally accepted classification).

From the disclosures discussed above, as summarised in WO97/12912, it has been concluded that essential to the membrane translocating properties of the homeodomain peptides, is the presence of a tryptophan residue as the sixth residue from the amino terminus. Conforming to these requirements has been a penetratin variant of the formula (KWKK)$_4$ (SEQ ID No. 64) which has been described as having translocating ability (Maruta H et al. Cytoskeletal tumour suppressors that block oncogenic RAS signalling. Presented at Anti-Cancer Proteins and Drugs: Structure, Function and Design; 6–9 Nov. 1998, New York Academy of Sciences. Poster/abstract No. 11) and Plank C et, al. (Human Gene Therapy, (1998) 10, 319–332) that discloses a number of branched membrane translocating peptides such as (KWKK)$_2$KGGC (SEQ ID No. 65), wherein each KWKK (SEQ ID No. 66) is joined to the following lysine residue.

SUMMARY

The present invention seeks to provide a wider range of membrane translocating peptides based on penetratin, including peptides that do not contain a tryptophan residue as the sixth residue from the amino terminus and peptides that are smaller in size than penetratin. Such smaller or truncated forms of penetratin are advantageous in that they are more acceptable to the pharmaceutical industry as delivery carrier moieties, by virtue of the carrier-cargo conjugate having a advantageous immunogenicity, solubility and clearance and in some cases advantageous efficacy as compared to using a conjugate comprised of "full length"

penetratin (SEQ ID No. 1). Thus, a first aspect of the present invention relates to truncated penetratin derivatives, whereas a second aspect relates to modified forms of penetratin. These first and second aspects are described below in greater detail and are both hereinafter referred to a the "carrier moiety" of a cargo delivery system.

A first aspect of the present invention therefore relates to a membrane translocation peptide carrier moiety of formula;

RQIKIWFQNRRMKWKK (SEQ ID NO. 1)
1                   16 wherein at least one amino acid residue is deleted from the amino terminus, or variants thereof. Thus, it has been surprisingly observed that contrary to the teaching of the prior art, the ability to translocate a cell membrane is retained with sequences not containing the whole of residues 43–58 of the pAntp peptide.

In accordance with the present invention up to 9 amino acids may be deleted from the amino terminus, preferably from 6 to 9 amino acids are deleted.

In a preferred embodiment, the peptide carrier moieties of the present invention include compounds 2 to 20 shown in Table 1 below where they are shown together with a biotinyl-βAla handle used for the purposes of biochemical assay. In a more preferred embodiment the peptide is compound 16, 17, 18 or 19.

Thus, in a preferred embodiment the carrier moiety includes the peptide sequence RRMKWKK (SEQ ID No. 2) or a variant thereof and may preferably be defined as a membrane translocation peptide carrier moiety comprising up to 15 amino acid residues and at least the peptide of formula;

RRMKWKK (SEQ ID NO. 2)     (I)
1      7 or variants thereof. The preferred embodiments discussed in relation to the first aspect apply in their entirety to the peptide of formula (I). In one embodiment, the amino acid residues added to the peptide of formula (I) are those corresponding residues in penetratin, or variants thereof.

This sequence (of formula (I)) and its variants have been observed to be the minimum sequence of the penetratin molecule necessary to facilitate membrane translocation. Thus, the above embodiments support the view that the presence of tryptophan at the sixth position from either end of the peptide is not essential for membrane translocation.

Within the above definitions of the peptide carrier moieties of the present invention, the specific amino acid residues of the peptide may be modified in such a manner that retains their ability to translocate, such modified peptides are referred to as "variants".

A variant of a carrier moiety as defined above includes any variation wherein; (a) one or more amino acid residues are replaced by a naturally or non-naturally occurring amino acid residue (b) the order of two or more amino acid residues is reversed, (c) both (a) and (b) are present together, (d) a spacer group is present between any two amino acid residues, (e) one or more amino acid residues are in peptoid form, (f) the (N—C—C) backbone of one or more amino acid residues of the peptide has been modified, or any of (a)–(f) in combination. Preferably, the variants arise from one of (a), (b) or (c).

Thus, homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine, a more detailed list of which appears below. Within each peptide carrier moiety more than one amino acid residue may be modified at a time.

As used herein, amino acids are classified according to the following classes;
basic; H, K, R
acidic; D, E
non-polar; A, F, G, I, L, M, P, V, W
polar; C, N, Q, S, T, Y,
(using the internationally accepted single letter amino acid notation) and homologous and non-homologous substitution is defined using these classes. Thus, homologous substitution is used to refer to substitution from within the same class, whereas non-homologous substitution refers to substitution from a different class or by an unnatural amino acid.

Suitable spacer groups that may be inserted between any two amino acid residues of the carrier moiety include alkyl groups such as methyl, ethyl or propyl groups in addition to amino acid spacers such as glycine or β-alanine residues. A further form of variation, type (e), involving the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367–9371 and Horwell D C, Trends Biotechnol. (1995) 13(4), 132–134. Type (f) modification may occur by methods such as those described in International Application PCT/GB99/01855.

Within the definition of formula (I) it has been demonstrated that it is preferable for amino acid variation, preferably of type (a) or (b), to occur independently at any of positions 1, 2, 3, 5 or 6. More preferably, amino acid variation occurs at positions 3 or 7, especially 3. Homologous substitution has been found to be preferable at positions 1 and 2, whereas positions 3, 4, 5 and 6 have surprisingly been observed to accept non-homologous substitution. As mentioned above more than one homologous or non-homologous substitution may occur simultaneously, for example at positions 2 and 3, 4 and 5 or 5 and 6. Further variation may occur by virtue of reversing the sequence of a number of amino acid residues within a sequence. For example in the peptide sequence RRMKWKK (SEQ ID No. 2), the lysine and tryptophan residues may be reversed to give a peptide RRMWKKK (SEQ ID No. 3). This modification may additionally occur in combination with a homologous or non-homologous substitution, for example, the sequence RROKWKK (SEQ ID No. 4) giving rise to RROWKKK (SEQ ID No. 5).

The carrier moiety may include further amino acid residues at the amino terminal end, more preferably by the addition of from 1 to 3 amino acid residues. Thus, a further embodiment of this aspect of the present invention relates to a peptide selected from RRMKWKK (SEQ ID No. 2), NRRMKWKK (SEQ ID No. 6), QNRRMKWKK (SEQ ID No. 7) and FQNRRMKWKK (SEQ ID No. 8).

In the most preferred embodiment of the first aspect of the invention, the truncated form of penetratin is of formula (I) described above or more preferably to a 7 amino acid peptide selected from KRMKWKK (SEQ ID No. 9), RKMKWKK (SEQ ID No. 10), RREKWKK (SEQ ID No. 11), RRQKWKK (SEQ ID No. 12), RROKWKK (SEQ ID No. 4), RRMKQKK (SEQ ID No. 13), RRMKWFK (SEQ ID No. 14), RORKWKK (SEQ ID No. 15), RRMWKKK (SEQ ID No. 16), RROWKKK (SEQ ID No. 5), RRMKKWK (SEQ ID No. 17) and RROKKWK (SEQ ID No. 18), most preferably, the peptide carrier moiety is RRMKWKK (SEQ ID No. 2).

A second aspect of the present invention relates to a membrane translocation peptide carrier moiety of formula;

RQIKIWFQNRRMKWKK (SEQ ID NO. 1)
1                                16 wherein at least one amino acid residue is replaced by an alternative natural or unnatural replacement amino acid residue.

In a preferred embodiment of the second aspect of the present invention, the sixth amino acid residue from the amino terminus of the peptide is not tryptophan. As will be described below, is has been demonstrated that the prevalent accepted principle that tryptophan must be present at this position is unfounded and hence a wider range of membrane translocating peptides has been identified.

In a preferred embodiment, the peptide carrier moieties of the present invention includes compounds 21 to 36 in (SEQ ID Nos.) shown in Table 3 below where they are shown together with a biotinyl-βAla handle used for the purposes of biochemical assay. In a more preferred embodiment the peptide is compound such as compound 26, wherein the sixth amino acid from the amino terminus is not tryptophan.

In one embodiment the replacement amino acid residue is selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. The replacement amino acid residue may additionally be selected from unnatural amino acids. Within the above definitions of the peptide carrier moieties of the present invention, the specific amino acid residues of the peptide may be modified in such a manner that retains their ability to translocate, such modified peptides are referred to as "variants".

A variant of a carrier moiety as defined above includes any variation wherein; (a) one or more amino acid residues are replaced by a naturally or non-naturally occurring amino acid residue (b) the order of two or more amino acid residues is reversed, (c) both (a) and (b) are present together, (d) a spacer group is present between any two amino acid (e) one or more amino acid residues are in peptoid form, (f) the (N—C—C) backbone of one or more amino acid residues of the peptide has been modified, or any of (a)–(f) in combination. Preferably, the variants arise from one of (a), (b) or (c).

Thus, homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Within each peptide carrier moiety more than one amino acid residue may be modified at a time.

As used herein, amino acids are classified according to the following classes;
basic; H, K, R
acidic; D, E
non-polar; A, F, G, I, L, M, P, V, W
polar; C, N, Q, S, T, Y,
(using the internationally accepted single letter amino acid notation) and homologous and non-homologous substitution is defined using these classes. Thus, homologous substitution is used to refer to substitution from within the same class, whereas non-homologous substitution refers to substitution from a different class or by an unnatural amino acid.

Suitable spacer groups that may be inserted between any two amino acid residues of the carrier moiety include alkyl groups such as methyl, ethyl or propyl groups in addition to amino acid spacers such as glycine or β-alanine residues. A further form of variation, type (e), involving the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367–9371 and Horwell D C, Trends Biotechnol. (1995) 13(4), 132–134.

Further non-natural amino acid derivatives that may be used in the context of the either the first or second aspects of the present include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, B-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above, to indicate the hydrophobic nature of the derivative whereas # has been utilised to indicate the hydrophilic nature of the derivative, #* indicates amphipathic characteristics.

The peptide carrier moieties of the present invention may comprise amino acids in the L or D form, i.e. one or more residues, preferably all the residues may be in the L or D form. Within this embodiment, the peptide may be in the retro form for example, the peptide KKWKORR (SEQ ID No. 36).

In a preferred embodiment of the present invention, the sixth amino acid residue from the amino terminus of the peptide is not tryptophan.

The membrane translocation peptides of the present invention are capable of translocating the cell membrane and in a preferred embodiment, also the nuclear membrane. It is irrelevant whether the peptide translocates from the exterior of the cell/nucleus or from the interior, i.e. the peptides may originate within the cytoplasm or nucleus (for example, by virtue of having being synthesised there or inserted into that compartment), and translocate to a location exterior to the cellular compartment (cytoplasm or nucleus) it originates from. In general, the peptides are prepared outside the cell and translocate from an exterior location to the cytoplasm and then optionally, on into the nucleus.

As used herein, the term "cell membrane translocation" refers to the ability of the peptide to cross the cell membrane and enter the cytosol/cytoplasm of a cell or to cross from the cytosol/cytoplasm of a cell to the exterior, extra-cellular or interstitial space.

The term "nuclear membrane translocation" refers to the ability of the peptide to cross the membrane structure surrounding the cell nucleus, or to cross from the cytosol/cytoplasm of a cell to the nucleus.

DETAILED DESCRIPTION

Figure 1:
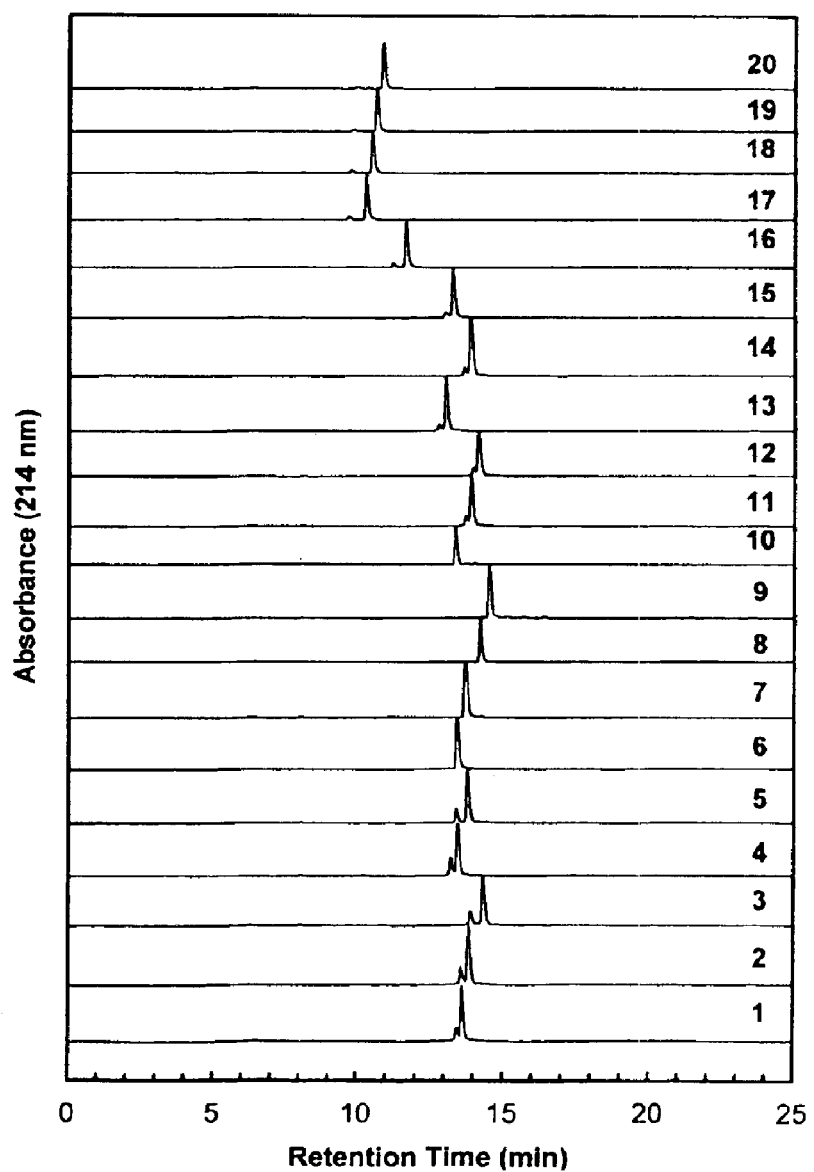
FIG. 1 shows the RP-HPLC analysis of some of the peptide carrier moieties prepared in accordance with the first aspect of the present invention.

In a further aspect of the invention, a peptide carrier moiety (either the truncated or modified form of penetratin in accordance with either the first or second aspects) is linked to a cargo moiety to form a cell translocation vector. The cargo moiety may comprise oligonucleotides, nucleotides, proteins, peptides, biologically active compounds, diagnostic agents or combinations thereof.

In a preferred embodiment the cargo moiety is a protein or peptide and in a more preferred embodiment the cargo moiety is a biologically active agent such as a drug.

The cargo moiety may be directly or indirectly linked to the carrier moiety. In the embodiment wherein the cargo moiety is indirectly linked to the carrier, the linkage may be by an intermediary bonding group such as a sulphydryl or carboxyl group or any larger group, all such linking groups are herein referred to as linker moieties as discussed below. Preferably, the carrier and cargo moieties are linked directly.

Examples of suitable oligonucleotide cargo moieties include genes, gene fragments, sequences of DNA, cDNA, RNA, nucleotides, nucleosides, heterocyclic bases, synthetic and non-synthetic, sense or anti-sense oligonucleotides including those with nuclease resistant backbones etc. or any of the above incorporating a radioactive label, that are desired to be delivered into a cell or alternatively to be delivered from a cell to its exterior. Preferably, the oligonucleotide cargo moiety is a gene or gene fragment.

Examples of suitable protein or peptide cargo moieties include; proteins, peptides, and their derivatives such as: antibodies and fragments thereof, cytokines and derivatives or fragments thereof, for example, the interleukins (IL) and especially the IL-1, IL-2, IL-3, IL-4, IL-5, IL-6, IL-7, IL-8, IL-9, IL-10, IL-11 and IL-12 subtypes thereof; colony stimulating factors, for example granulocyte-macrophage colony stimulating factor, granulocyte-colony stimulating factor (alpha and beta forms), macrophage colony stimulating factor (also known as CSF-1); haemopoietins, for example erythropoietin, haemopoietin-alpha and kit-ligand (also known as stem cell factor or Steel factor); interferons (IFNS), for example IFN-α, IFN-β and IFN-γ; growth factors and bifunctional growth modulators, for example epidermal growth factor, platelet derived growth factor, transforming growth factor (alpha and beta forms), amphiregulin, somatomedin-C, bone growth factor, fibroblast growth factors, insulin-like growth factors, heparin binding growth factors and tumour growth factors; differentiation factors and the like, for example macrophage differentiating factor, differentiation inducing factor (DIF) and leukaemia inhibitory factor; activating factors, for example platelet activating factor and macrophage activation factor; coagulation factors such as fibrinolytic/anticoagulant agents including heparin and proteases and their pro-factors, for example clotting factors VII, VIII, IX, X, XI and XII, antithrombin III, protein C, protein S, streptokinase, urokinase, prourokinase, tissue plasminogen activator, fibrinogen and hirudin; peptide hormones, for example insulin, growth hormone, gonadotrophins, follicle stimulating hormone, leutenising hormone, growth hormone releasing hormone and calcitonin; enzymes such as superoxide dismutase, glucocerebrosidase, asparaginase and adenosine deaminase; vaccines or vaccine antigens such as, for example hepatitis-B vaccine, malaria vaccine, melanoma vaccine and HIV-1 vaccine; transcription factors and transcriptional modulators. More preferably, the cargo may be a protein or peptide selected from proteins or peptides that interfere with the cell cycle, such as p53 peptides or fragments thereof, p21$^{WAF}$ peptides or fragments thereof such as those described in WO96/14334 and WO97/42222, Fen1 peptides or fragments thereof such as those described in WO96/35715, p16 peptides or fragments thereof such as those described in WO97/11174 and fragments and derivatives thereof.

Examples of a suitable non-nucleotide/proteinaceous biologically active cargo moieties are drug moieties selected from cytotoxic agents, anti-neoplastic agents, anti-hypertensives, cardioprotective agents, anti-arrhythmics, ACE inhibitors, anti-inflammatory's, diuretics, muscle relaxants, local anaesthetics, hormones, cholestrol lowering drugs, anti-coagulants, anti-depressants, tranquilizers, neuroleptics, analgesics such as a narcotic or anti-pyretic analgesics, anti-virals, anti-bacterials, anti-fungals, bacteriostats, CNS active agents, anti-convulsants, anxiolytics, antacids, narcotics, antibiotics, respiratory agents, anti-histamines, immunosuppressants, immunoactivating agents, nutritional additives, anti-tussives, diagnostic agents, emetics and anti-emetics, carbohydrates, glycosoaminoglycans, glycoproteins and polysaccharides; lipids, for example phosphatidyl-ethanolamine, phosphtidylserine and derivatives thereof; sphingosine; steroids; vitamins; antibiotics including lantibiotics; bacteristatic and bactericidal agents; antifungal, anthelminthic and other agents effective against infective agents including unicellular pathogens; small effector molecules such as noradrenalin, alpha adrenergic receptor ligands, dopamine receptor ligands, histamine receptor ligands, GABA/benzodiazepine receptor ligands, serotonin receptor ligands, leukotrienes and triodothyronine; cytotoxic agents such as doxorubicin, methotrexate and derivatives thereof.

Preferably the drug moiety is a cytotoxic or anti-neoplastic agent, particularly those which are used for cancer therapy. Such drugs include, in general, DNA damaging agents, anti-metabolites, anti-tumour antibiotics, natural products and their analogues, dihydrofolate reductase inhibitors, pyrimidine analogues, purine analogues, cyclin-dependent kinase inhibitors, thymidylate synthase inhibitors, DNA intercalators, DNA cleavers, topoisomerase inhibitors, anthracyclines, vinca drugs, mitomycins, bleomycins, cytotoxic nucleosides, pteridine drugs, diynenes, podophyllotoxins, platinum containing drugs, differentiation inducers, and taxanes. Particularly useful members of those classes include, for example, methotrexate, methopterin, dichloromethotrexate, 5-fluorouracil, 6-mercaptopurine, tri-substituted purines such as olomoucine, roscovitine and bohemine, flavopiridol, staurosporin, cytosine arabinoside, melphalan, leurosine, actinomycin, daunorubicin, doxorubicin, mitomycin D, mitomycin A, carninomycin, aminopterin, tallysomycin, podophyllotoxin, etoposide, cisplatin, carboplatinum, vinblastine, vincristine, vindesin, paclitaxel, docetaxel, taxotere retinoic acid, butyric acid, acetyl spermidine, tamoxifen, irinotecan and camptothecin. Most preferably the drug is selected from olomoucine, roscovitine and bohemine, flavopiridol, staurosporin, and podophyllotoxin, etoposide, purvalanol derivatives, taxol, paclitaxel and camptothecin.

As discussed above the drug and carrier moieties may be linked directly or indirectly via a linker moiety. Direct linkage may occur through any convenient functional group on the drug moiety such as a hydroxy, carboxy or amino group. Indirect linkage which is preferable, will occur through a linking moiety. Suitable linking moieties include bi- and multi-functional alkyl, aryl, aralkyl or peptidic moieties, alkyl, aryl or aralkyl aldehydes acids esters and anyhdrides, sulphydryl or carboxyl groups, such as maleimido benzoic acid derivatives, maleimido proprionic acid derivatives and succinimido derivatives or may be derived from cyanuric bromide or chloride, carbonyldiimidazole, succinimidyl esters or sulphonic halides and the like. The functional groups on the linker moiety used to form covalent bonds between linker and drugs on the one hand, as well as linker and carrier moiety on the other hand, may be two or more of, e.g., amino, hydrazino, hydroxyl, thiol, maleimido, carbonyl, and carboxyl groups, etc. The linker moiety may include a short sequence of from 1 to 4 amino acid residues that optionally includes a cysteine residue through which the linker moiety bonds to the carrier moiety.

In accordance with the present invention each carrier moiety may be linked to at least one drug moiety. In a further embodiment, the carrier moiety is prepared such as to facilitate linkage to more than one cargo moiety, each cargo moiety being the same or different. For example, the carrier moiety may comprise components that themselves facilitate the attachment of more than one cargo moiety such as derivatives of naturally occurring amino acids or insertion of a multi-valent synthetic amino acid, or it may be specifically adapted to do so for example by a network of branched lysine residues that may be attached to the carrier moiety as a linking group and each lysine residue may then be attached to a cargo moiety. In this manner a single carrier moiety may carry up to 32 cargo moieties, preferably from 2 to 10 or more preferably from 4 to 5 cargo moieties. In this further embodiment each cargo moiety may be directly or indirectly linked to the carrier moiety. When more than one different type of cargo moiety is attached, it is possible to co-ordinate the ratios and dosages of the individual drugs to facilitate the administration of specific cargo combinations.

In a preferred example of this embodiment, the carrier moiety is peptide carrier moiety as defined above, with a network of lysine residues attached to at least one end facilitating the attachment of up to 32 cargo moieties.

In a further embodiment, the translocation vector may further comprise a targeting moiety. The targeting moiety is capable of directing the carrier moiety to the specific cell type to which it is preferable for the cargo moiety to function. Thus, the targeting moiety acts as an address system biasing the bodies natural distribution of drugs or the delivery system to a particular cell type. The targeting moiety may be attached to the cargo moiety or more preferably to the carrier moiety and will direct the delivery system to a desired site, upon arrival at which the carrier moiety will facilitate the cellular internalisation of the cargo. Suitable targeting moieties include the peptide sequences identified by E Ruoslahti et al. in U.S. Pat. No. 5,622,699; Pasqualini, R, Ruoslahti, E. Nature (London) (1996), 380, 364–366, Ruoslahti, E. Ann. Rev. Cell Dev. Biol. (1996), 12, 697–715; Arap, W, Pasqualini, R, Ruoslahti, E, Science (1998), 279, 377–380. These disclosures, which are herein incorporated by reference, describe certain peptides that have been found to act as address labels to certain cell types.

In accordance with any of the above defined embodiments of the present invention, the amino acids (any number thereof, but preferably all of them) comprising the peptide carrier moiety may be in the L or D (inverso) form. More preferably they are in the L form.

In a further embodiment the carrier moiety as previously described may be in the retro form. Within this further embodiment, the amino acids (any number thereof, but preferably all of them) comprising the peptide carrier moiety may be in the L or D form.

When the cargo moiety is itself a protein or peptide, the carrier and cargo moieties may both be in the L or D forms or alternatively the carrier may be in the L form and the cargo in the D form or the carrier in the D form and the cargo in the L form.

Within the carrier moieties defined as penetratin or derivatives thereof, a further modification that is beneficial in the context of the present invention is conversion of the free carboxyl group of the carboxy terminal amino acid residue, to an carboxamide group. By way of example, when the carrier moiety is of formula I (RRMKWKK (SEQ ID No. 2)) the carboxy terminal lysine residue may have its carboxyl group converted into an carboxamide group. This modification is believed to enhance the stability of the carrier moiety and hence the delivery system as a whole. Thus, the C-terminal amino acid residue may be in the form —C(O)—NRR', wherein R and R' are each independently selected from hydrogen, C1–6 alkyl, C1–6 alkylene or C1–6 alkynyl (collectively referred to "alk"), aryl such as benzyl or alkaryl, each optionally substituted by heteroatoms such as O, S or N. Preferably at least one of R or R' is hydrogen, most preferably, they are both hydrogen.

Thus, its most preferred embodiment, the present invention relates to a carrier moiety RRMKWKK (SEQ ID No. 2) with an optionally amidated terminal lysine residue, directly worked to a cargo moiety selected from $p21^{WAF}$ derived peptides, p16 derived peptides or the drugs, roscovitine, taxol or a podophyllotoxin.

The delivery systems described herein are novel chemical entities. Specific chemical entities disclosed herein include:

| # | Drug moiety | Linker moiety | Carrier moiety |
|---|---|---|---|
| | paclitaxel | 2'-succinimidopropionoyl-CβA | RRMKWKK-NH$_2$ (Seq ID No. 2) |
| | podophyllotoxin | 4-succinimidopropionoyl-CβA | RRMKWKK-NH$_2$ (Seq ID No. 2) |
| | podophyllotoxin | 4-succinimidopropionoyl-CβA | (D-R)(D-R)(D-M)(D-K)(D-W)(D-K)(D-K-NH$_2$) (Seq ID No. 2) |
| | epipodophyllotoxin | 4'-succinimidopropionoyl-CβA | RRMKWKK-NH$_2$ (Seq ID No. 2) |
| | podophyllotoxin | 4-acetyl-CβA | RRMKWKK-NH$_2$ (Seq ID No. 2) |
| | 4'-demethyl epipodophyllotoxin | 4-acetyl-CβA | RRMKWKK-NH$_2$ (Seq ID No. 2) |
| | podophyllotoxin | 4-succinimidopropionoyl-GCβA | RRMKWKK-NH$_2$ (Seq ID No. 2) |
| C-term | podophyllotoxin | 4-succinimidopropionoyl-C | RRMKWKK (Seq ID No. 2) |
| N-term | podophyllotoxin | 4-succinimidopropionoyl-C | |
| N-term | epipodophyllotoxin | 4'-succinimidopropionoyl-C | RRMKWKK (Seq ID No. 2) |
| C-term | camptothecin | 10-O-succinimidopropionoyl-C | |
| N-term | epipodophyllotoxin | 4'-succinimidopropionoyl-C | RRMKWKK (Seq ID No. 2) |
| C-term | paclitaxel | 2'-(succinimido)propionoyl-C | |
| | 4'-methoxy-epipodophyllotoxin | 4-(4''-aminoanilino)succinimidopropionoyl-CβA | RRMKWKK-NH$_2$ (Seq ID No. 2) |
| | 4'-demethyl-epipodophyllotoxin | 4-(4''-aminoanilino)succinimidopropionoyl-CβA | RRMKWKK-NH$_2$ (Seq ID No. 2) |

The therapeutic effect resulting from the administration of the delivery system may arise from the intact delivery system or any of its dissociated components that include the cargo moiety i.e the cargo moiety alone or bound to the linker, part of the linker or the linker and part of the carrier. Thus the term "delivery system" has been used herein to have its ordinary meaning i.e that of delivering something such as the cargo moiety and additionally to include the system or any portion thereof as being active in its intact state. Thus, the benefits provided by the system discussed above are applicable to the cargo and delivery system.

The delivery vectors may be prepared by any methods known in the art. For example, the carrier moiety peptide can be assembled using conventional solution- or solid-phase peptide synthesis methods, affording a fully protected precursor with only the terminal amino group in deprotected reactive form. This function can then be reacted directly with a cargo moiety or a suitable reactive derivative of a cargo moiety. Alternatively, this amino group may be converted into a different functional group suitable for reaction with a cargo moiety or a linker. Thus, e.g. reaction of the amino group with succinic anhydride will provide a selectively addressable carboxyl group, while further peptide chain extension with a cysteine derivative will result in a selectively addressable thiol group. Once a suitable selectively addressable functional group has been obtained in the delivery vector precursor, a cargo moiety or a derivative thereof may be attached through e.g. amide, ester, or disulphide bond formation. Alternatively, a linker group, e.g. m-maleimidobenzoyl, is introduced by reaction of a linker group precursor with the selectively addressable function of the delivery vector precursor, followed by formation of a covalent bond between the linker group and a cargo moiety. Multivalent cargo-delivery vector constructs may be obtained, inter alia, by successive extension of the selectively addressable delivery vector precursor with trivalent chemical groups. Thus peptide chain extension with e.g. N$^{\alpha,\epsilon}$-Fmoc-protected Lys derivatives will afford di-, tetra-, and octa-valent construct precursors after one, two, or three coupling/Fmoc-deprotection cycles.

Using these methods, the skilled person will be capable of preparing a wide variety of cargo-carrier conjugates utilising a variety of linker moieties. As exemplified below, an appropriate group on the cargo moiety may be selected for attachment to the carrier moiety and if desired a linker joined to the cargo or carrier moiety, or both prior to their coupling.

The compounds of the present invention may be formulated with a physiologically acceptable diluent or carrier for use as pharmaceuticals for both veterinary, for example in mammals, and particularly human use by a variety of methods. For instance, they may be applied as a composition incorporating a liquid diluent or carrier, for example an aqueous or oily solution, suspension or emulsion, which may often be employed in injectable form for parental administration and therefore may conveniently be sterile and pyrogen free. Oral administration may also be used and although compositions for this purpose may incorporate a liquid diluent or carrier, it is more usual to use a solid, for example a conventional solid carrier material such as starch, lactose, dextrin or magnesium stearate. Such solid compositions may take the form of powders but are more conveniently of a formed type, for example as tablets, cachets, or capsules (including spansules). Alternative, more specialized types of formulation include liposomes and nanoparticles.

Other types of administration than by injection or through the oral route which are of use in both human and veterinary contexts include the use of suppositores or pessaries. Another form of pharmaceutical composition is one for buccal or nasal administration or administration to the airways such as alveolar tissue. Other formulations of topical administration include lotions, ointments, creams, gels and sprays.

Compositions may be formulated in unit dosage form, i.e. in the form of discrete portions containing a unit does, or a multiple or sub-unit of a unit dose.

The translocation vectors of the present invention provides several advantages over known delivery systems. These advantages include improved efficacy compared to conventional treatments, improved cellular uptake of the therapeutic agent, improved water solubility, reduction of side effects and cellular bioavailablility and decreased occurrence of drug resistance.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Preparation of a Series of Peptides (Peptides 1–20), being Truncated Forms of Penetratin (SEQ ID No. 1)

Abbreviations.

Amino acid and peptide nomenclature conforms to IUPAC-IUB rules (*Eur. J. Biochem.* 1984, 138, 9–37). Other abbreviations: Ahx, 6-aminohexanoyl; APase, alkaline phosphatase. DE MALDI-TOF MS, delayed-extraction matrix-assisted laser desorption ionisation time-of-flight mass spectrometry. DIEA, N,N-diisopropylethylamine. PBS, phosphate-buffered saline (10 mM phosphate, 150 mM NaCl, pH 7.4); PyBOP, Benzotriazole-1-yl-oxy-tris-pyrrolidino-phosphonium hexafluorophosphate; RP-HPLC, reversed-phase high-performance liquid chromatography; TFA, trifluoroacetic acid.

1.1: Materials and Methods

General

The peptide deprotection/cleavage mixture used throughout was as follows: 0.75:0.5:0.5:0.25:10 (w/v/v/v/v) PhOH, $H_2O$, PhSMe, 1,2-ethanedithiol, TFA (Beavis, R. C. et al., (1992) Organic Mass Spectrometry 27, 156–158). Analytical and preparative RP-HPLC was performed using Vydac 218TP54 (4.6×250 mm) and 218TP1022 (22×250 mm) columns, respectively. Flow rates of 1 mL/min for analytical runs and 9 mL/min for preparative work were used (at 25° C.). Gradient elution with increasing amounts of MeCN in $H_2O$ (containing 0.1% TFA) over 20 min (anal.) and 40 min (prep.) was performed. Eluants were monitored at $\lambda$=200–300 nm. Peptide samples were also analysed by DE MALDI-TOF mass spectrometry (ThermoBioAnalysis Dynamo instrument). An α-cyano-4-hydroxycinnamic acid matrix (Beavis, R. C. et al., (1992) Organic Mass Spectrometry 27, 156–158) was used and the appropriate m/z range was calibrated using authentic peptide standards in the m/z range 1,000–2,600.

1.2: Simultaneous Multiple Synthesis of Peptides 1–20

Peptides were synthesised using a Multipin Peptide Synthesis Kit (Chiron Technologies Pty. Ltd., Clayton, VIC, Australia). Peptide chains were assembled on "Macro Crowns" (SynPhase HM Series I, Rink Amide Linker; 5.3 µmol/crown) using Fmoc-amino acids (100 mM in DMF) and PyBOP/HOBt)/DIEA (1:1:1.5) coupling chemistry. The amino acid side-chain protecting groups were 2,2,5,7,8-pentamethylchroman-6-sulphonyl (Arg), trityl (Asn and Gln), and t-butyloxycarbonyl (Lys and Trp). Activated amino acid solutions were dispensed using a PinAID device (Chiron Technologies). Coupling reactions were allowed to proceed for a minimum of 4 h. All other chain assembly manipulations, including repetitive deprotection reactions (20% piperidine in DMF) and washing cycles (DMF and MeOH), were carried out according to procedures set out in the kit manual. After coupling and deprotection of the N-terminal βAla residues, (+)-biotin (300 mM in DMF) was coupled (chemistry as above for amino acids) during 4 h. After washing and drying, the "Macro Crowns" were removed from the synthesis device and placed into 10-mL capped polypropylene tubes. To each tube was added 1.5 mL of cleavage/deprotection mixture. After 2 h, the "Macro Crowns" were removed and washed with 0.5 mL each of neat TFA. To each tube containing the combined cleavage mixtures and washings $Et_2O$ (8 mL) was added. After cooling to 4° C., the precipitated peptides were collected by centrifugation (4 min at 5,000 r.p.m.) and decantation. The pellets were resuspended in $Et_2O$ (5 mL/tube). The suspensions were again cooled and the peptides isolated as before. The washing process was repeated once more before the crude peptides were dried in vacuo.

The crude peptides were redissolved in 0.1% aq TFA using sonication (2 mL/sample) and were applied to primed (MeOH then 0.1% aq TFA) solid-phase extraction cartridges (Merck LiChrolut RP-18, 500 mg). These were successively washed (1×2 mL 0.1% aq TFA each) and eluted (2 mL 0.1% TFA in 6:4 MeCN/$H_2O$). The eluates were evaporated to dryness by vacuum centrifugation. Yields and analytical data for the title compounds are summarised in Table 2.

| N° | Peptide | |
|---|---|---|
| 1 | Biotinyl-βAla-Arg-Gln-Ile-Lys-Ile-Trp-Phe-Gln-Asn-Arg-Arg-Met-Lys-Trp-Lys-Lys-$NH_2$ | (Seq ID No. 19) |
| 2 | Biotinyl-βAla-Arg-Gln-Ile-Lys-Ile-Trp-Phe-Gln-Asn-Arg-Arg-Met-Lys-Trp-Lys-$NH_2$ | (Seq ID No. 37) |
| 3 | Biotinyl-βAla-Arg-Gln-Ile-Lys-Ile-Trp-Phe-Gln-Asn-Arg-Arg-Met-Lys-Trp-$NH_2$ | (Seq ID No. 38) |
| 4 | Biotinyl-βAla-Arg-Gln-Ile-Lys-Ile-Trp-Phe-Gln-Asn-Arg-Arg-Met-Lys-$NH_2$ | (Seq ID No. 39) |
| 5 | Biotinyl-βAla-Arg-Gln-Ile-Lys-Ile-Trp-Phe-Gln-Asn-Arg-Arg-Met-$NH_2$ | (Seq ID No. 40) |
| 6 | Biotinyl-βAla-Arg-Gln-Ile-Lys-Ile-Trp-Phe-Gln-Asn-Arg-Arg-$NH_2$ | (Seq ID No. 41) |
| 7 | Biotinyl-βAla-Arg-Gln-Ile-Lys-Ile-Trp-Phe-Gln-Asn-Arg-$NH_2$ | (Seq ID No. 42) |
| 8 | Biotinyl-βAla-Arg-Gln-Ile-Lys-Ile-Trp-Phe-Gln-Asn-$NH_2$ | (Seq ID No. 43) |
| 9 | Biotinyl-βAla-Arg-Gln-Ile-Lys-Ile-Trp-Phe-Gln-$NH_2$ | (Seq ID No. 44) |
| 10 | Biotinyl-βAla-Arg-Gln-Ile-Lys-Ile-Trp-$NH_2$ | (Seq ID No. 45) |
| 11 | Biotinyl-βAla-Gln-Ile-Lys-Ile-Trp-Phe-Gln-Asn-Arg-Arg-Met-Lys-Trp-Lys-Lys-$NH_2$ | (Seq ID No. 46) |
| 12 | Biotinyl-βAla-Ile-Lys-Ile-Trp-Phe-Gln-Asn-Arg-Arg-Met-Lys-Trp-Lys-Lys-$NH_2$ | (Seq ID No. 47) |
| 13 | Biotinyl-βAla-Lys-Ile-Trp-Phe-Gln-Asn-Arg-Arg-Met-Lys-Trp-Lys-Lys-$NH_2$ | (Seq ID No. 48) |
| 14 | Biotinyl-βAla-Ile-Trp-Phe-Gln-Asn-Arg-Arg-Met-Lys-Trp-Lys-Lys-$NH_2$ | (Seq ID No. 49) |
| 15 | Biotinyl-βAla-Trp-Phe-Gln-Asn-Arg-Arg-Met-Lys-Trp-Lys-Lys-$NH_2$ | (Seq ID No. 50) |
| 16 | Biotinyl-βAla-Phe-Gln-Asn-Arg-Arg-Met-Lys-Trp-Lys-Lys-$NH_2$ | (Seq ID No. 51) |
| 17 | Biotinyl-βAla-Gln-Asn-Arg-Arg-Met-Lys-Trp-Lys-Lys-$NH_2$ | (Seq ID No. 52) |
| 18 | Biotinyl-βAla-Asn-Arg-Arg-Met-Lys-Trp-Lys-Lys-$NH_2$ | (Seq ID No. 53) |
| 19 | Biotinyl-βAla-Arg-Arg-Met-Lys-Trp-Lys-Lys-$NH_2$ | (Seq ID No. 54) |
| 20 | Biotinyl-βAla-Arg-Met-Lys-Trp-Lys-Lys-$NH_2$ | (Seq ID No. 55) |

TABLE 2

Chromatographic and mass spectrometric analysis of peptides 1–20

| N° | Formula | MS[a] $M_r$ | MS[a] $[M + H]^+$ | Yield mg[b] | Yield μmol | Yield %[c] | Anal. RP-HPLC $t_R$ (min)[d] | Anal. RP-HPLC Purity (%)[e] |
|---|---|---|---|---|---|---|---|---|
| 1 | $C_{117}H_{188}N_{38}O_{22}S_2$ | 2543.12 | 2544.1 | 6.7 | 2.6 | 50 | 19.0 | 78 |
| 2 | $C_{111}H_{176}N_{36}O_{21}S_2$ | 2414.95 | 2416.0 | 6.8 | 2.8 | 53 | 19.4 | 78 |
| 3 | $C_{105}H_{1164}N_{34}O_{20}S_2$ | 2286.77 | 2287.8 | 4.8 | 2.1 | 40 | 20.3 | 79 |
| 4 | $C_{94}H_{154}N_{32}O_{19}S_2$ | 2100.56 | 2101.6 | 7.5 | 3.6 | 67 | 18.5 | 75 |
| 5 | $C_{88}H_{142}N_{30}O_{18}S_2$ | 1972.39 | 1973.4 | 6.5 | 3.3 | 62 | 19.1 | 81 |
| 6 | $C_{83}H_{133}N_{29}O_{17}S$ | 1841.20 | 1842.2 | 5.6 | 3.1 | 58 | 18.5 | 98 |
| 7 | $C_{77}H_{121}N_{25}O_{16}S$ | 1685.01 | 1686.0 | 7.0 | 4.2 | 78 | 19.0 | 95 |
| 8 | $C_{71}H_{109}N_{21}O_{15}S$ | 1528.82 | 1529.8 | 4.8 | 3.1 | 59 | 19.7 | 95 |
| 9 | $C_{67}H_{103}N_{19}O_{13}S$ | 1414.72 | 1415.7 | 4.8 | 3.4 | 64 | 20.2 | 90 |
| 10 | $C_{53}H_{86}N_{16}O_{10}S$ | 1139.42 | 1140.4 | 3.2 | 2.8 | 53 | 17.9 | 93 |
| 11 | $C_{111}H_{176}N_{34}O_{21}S_2$ | 2386.93 | 2387.9 | 5.1 | 2.1 | 40 | 19.5 | 82 |
| 12 | $C_{106}H_{168}N_{32}O_{19}S_2$ | 2258.80 | 2259.8 | 5.0 | 2.2 | 42 | 19.8 | 85 |
| 13 | $C_{100}H_{157}N_{31}O_{18}S_2$ | 2145.65 | 2146.7 | 5.8 | 2.7 | 51 | 17.6 | 90 |
| 14 | $C_{94}H_{145}N_{29}O_{17}S_2$ | 2017.47 | 2018.5 | 6.6 | 3.3 | 62 | 19.1 | 87 |
| 15 | $C_{88}H_{134}N_{28}O_{16}S_2$ | 1904.32 | 1905.3 | 5.3 | 2.8 | 53 | 17.9 | 90 |
| 16 | $C_{77}H_{124}N_{26}O_{15}S_2$ | 1718.11 | 1719.1 | 5.3 | 3.1 | 58 | 14.9 | 91 |
| 17 | $C_{68}H_{115}N_{25}O_{14}S_2$ | 1570.93 | 1571.9 | 5.6 | 3.6 | 67 | 12.2 | 93 |
| 18 | $C_{63}H_{107}N_{23}O_{12}S_2$ | 1442.80 | 1443.8 | 4.4 | 3.0 | 57 | 12.4 | 93 |
| 19 | $C_{59}H_{101}N_{21}O_{10}S_2$ | 1328.70 | 1329.7 | 5.1 | 3.9 | 73 | 12.7 | 94 |
| 20 | $C_{53}H_{89}N_{17}O_9S_2$ | 1172.51 | 1173.5 | 5.0 | 4.3 | 81 | 13.2 | 96 |

[a]By DE MALDI-TOF MS.
[b]After solid-phase extraction and vacuum centrifugation.
[c]Relative to 5.3 μmol loading of synthesis 'crowns'.
[d]Gradient 5–35% (peptides 1–20) in 0.1% aq TFA over 20 min.
[e]From chromatogram integration (λ = 214 nm).

Preparation of Reduced Linear and Oxidised Cyclic Peptides 37 and 38

The peptide sequence was assembled on Fmoc-Cys(Trt)-resin (p-hydroxymethylphenoxyacetic acid handle, 0.50 mmol/g functionality, 0.50 g, 0.25 mmol; ABI 401418) using an ABI 433A Peptide Synthesizer (Perkin-Elmer Applied Biosystems) and standard "0.25 mmol FastMoc MonPrevPk" chemistry. After final Fmoc-deprotection and washing (Et$_2$O), the peptidyl resin was dried in vacuo (1.43 g, 91%). An aliquot (285 mg, ca. 0.05 mmol) of this material was resuspended in DMF, drained, and reacted with biotinamidocaproate N-hydroxysuccinimide ester (137 mg, 0.3 mmol), HOBt (50 mg, 0.3 mmol) and DIEA (0.14 mL 0.8 mmol) in DMF (3 mL) for 18 h under N$_2$. The resin was then washed successively with DMF, CH$_2$Cl$_2$ and Et$_2$O, before being dried in vacuo.

The above biotinylated peptidyl resin (290 mg, ca. 0.05 mmol) was treated with cleavage/deprotection mixture (5 mL) for 2.5 h. Resin residue was then filtered off. The filtrate was treated with Et$_2$O (45 mL), the mixture was cooled and the precipitated peptide was collected by centrifugation (2 min at 4,000 r.p.m.). The crude biotinylated peptide (141 mg, ca. quant.) was washed twice more with Et$_2$O in a similar manner before being dried in vacuo. A sample (20 mg) of this material was dissolved in 0.1% aq TFA (2 mL), the solution was filtered and fractionated by prep. RP-HPLC. Fractions containing pure material (by anal. RP-HPLC) were pooled and lyophilised to afford pure peptide 37 (12.1 mg). Anal. RP-HPLC: $t_R$=20.8 min, purity>99% at λ=214 nm (20–30% MeCN gradient). DE MALDI-TOF MS: [M+H]$^+$=2776, [2 M+H]$^{2+}$=1389 ($C_{127}H_{205}N_{39}O_{25}S_3$=2774.43).

Crude peptide 37 (before prep. RP-HPLC, 35 mg) was dissolved in aq NH$_4$HCO$_3$ solution (0.1 M, 70 mL). The uncapped mixture was stirred for 18 h at room temperature. The resulting suspension was then acidified to pH 4 with AcOH (ca. 2 mL) to yield a clear solution which was evaporated to dryness by vacuum centrifugation for 18 h. The residue was redissolved in 0.1% aq TFA (2 mL) and purified by prep. RP-HPLC in a similar manner to the above reduced precursor 37 except that the gradient was developed from 20–30% MeCN. After lyophilisation, pure peptide 38 (4.5 mg) was obtained. Anal. RP-HPLC: $t_R$=15.7 min, purity>99% at λ=214 nm (20–30% gradient). DE MALDI-TOF MS: [M+H]$^+$=2774, [2 M+H]$^{2+}$=1388 ($C_{27}H_{203}N_{39}O_{25}S_3$=2772.42).

Preparation of Fluorescein-labelled Penetratin 39

The sequence was assembled in a similar fashion as described for peptide 37, except that Fmoc-Lys(Boc)-Resin (0.5 mmol/g loading; ABI 401425) was used. The H-βAla-Arg(Pmc)-Gln(Trt)-Ile-Lys(Boc)-Ile-Trp-Phe-Gln(Trt)-Asn(Trt)-Arg(Pmc)-Arg(Pmc)-Met-Lys(Boc)-Trp-Lys(Boc)-Lys(Boc)-Resin (SEQ ID No. 19) (300 mg, ca. 0.055 mmol) was reacted with 5-carboxyfluorescein (103 mg, 0.27 mmol; Sigma C 0537), PyBOP (142 mg, 0.27 mmol)), HOBt (37 mg, 0.27 mmol), and DIEA (71 mL, 0.41 μmol) in DMF (5 mL) under N$_2$ and in the dark during 18 h. It was then washed (DMF, CH$_2$Cl$_2$, and Et$_2$O) and dried in vacuo. After treatment during 2 h with cleavage/deprotection mixture (12 mL) in the dark and work-up as above, crude peptide was obtained (183 mg). An aliquot (90 mg) was purified by preparative RP-HPLC to afford pure peptide after lyophilisation (38 mg). Anal. RP-HPLC: $t_R$=15.7 min, purity>99% at λ=214 nm (22.5–32.5% gradient). DE MALDI-TOF MS: $[M+H]^+$=2677, $[2\ M+H]^{2+}$=5359 ($C_{128}H_{183}N_{35}O_{27}S$=2676.11).

1.3: Peptide Internalisation Assay

HaCaT cells (immortalised 'normal' human fibroblast cell line) were seeded into 96-well plates at 50,000 cells per well in medium (DMEM) with 10% foetal calf serum and antibiotics. After an overnight incubation, peptides were prepared as dilution series in cell medium and were added to the cells. At the end of the incubation period (usually 10 and 60 min), the cells were rinsed three times with PBS and fixed for 20 min at −20° C. in EtOH/AcOH (95:5). After the fixation, the cells were made permeable by treatment for 10 min with PBS containing 3% Tween-20. Endogenous alkaline phosphatase activity was neutralised by incubation at 65° C. for 60 min. Cells were incubated for 30 min at room temperature with alkaline phosphatase-streptavidin (Pierce Chemical Co., Rockford, Ill., USA) in 0.1% BSA in PBS and washed extensively with PBS. Freshly prepared substrate solution (1 mg/mL p-nitrophenyl phosphate disodium (Pierce Chemical Co.) in 10 mM diethanolamine (pH 9.5) containing 0.5 mM $MgCl_2$ was added to each well and incubated until sufficient colour had developed (approximately 30 min.). The enzymatic reaction was stopped by adding 50 μL 2 M aq NaOH to each well. Alkaline phosphatase activity was measured spectrophotometrically at 405 nm.

1.4: Results 1.4.1: Peptide Synthesis

Peptides 1–20 were prepared simultaneously using the so-called Multipin™ method (Valerio, R. M. et al., (1993) International Journal of Peptide and Protein Research 42, 1–9). On average 2 coupling/deprotection cycles were performed per day and the entire synthesis, including biotinylation, cleavage/deprotection, purification by solid phase extraction, and analysis, were completed within a fortnight. The isolated and purified yields of the peptides ranged from 40–81% and purities were 75–96% (Table 2). The excellent quality of the peptides is demonstrated in FIG. 1. The main impurities observed (MS, data not shown) were Met(O)-containing peptides (leading peaks on traces in FIG. 1. Methionine sulfoxide formation appears to be a general problem attendant in the Multipin method, presumably due to oxidation during the extended air drying cycles after the acylation and deprotection steps. In principle it is possible to back-reduce Met(O) in peptides; e.g., on an analytical scale we were able to convert the Met(O)-containing impurity to 1 cleanly using $NH_4I/Me_2S$ in TFA (Nicolás, E et al., (1995) Tetrahedron 51, 57013) (results not shown).

1.4.2: Determination of Minimal Active Sequence

Figure 2:
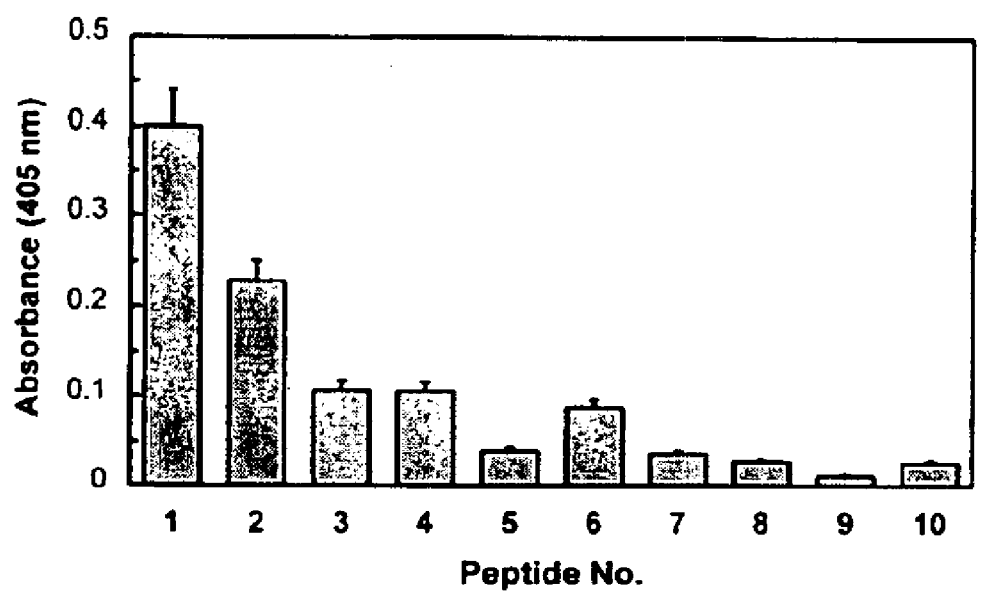
FIG. 2 shows the results of the cell internalisation assay performed using peptide carrier moieties prepared in accordance with the first aspect of the invention.
Figure 2:
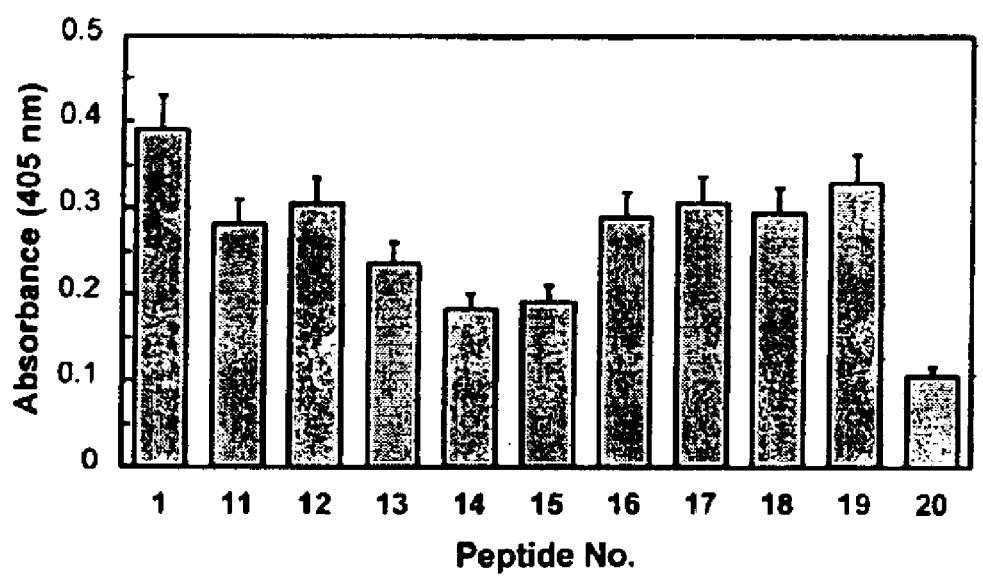
Figure 3:
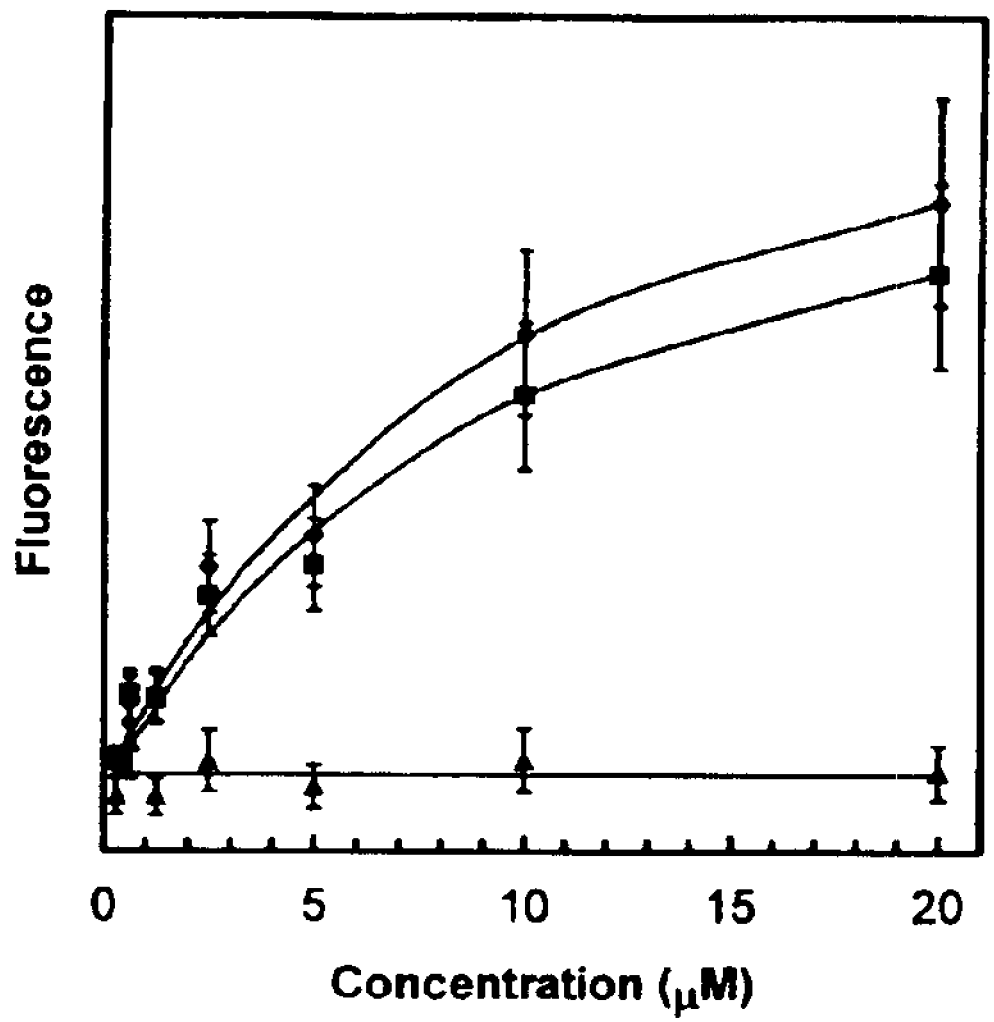
FIG. 3 shows the results of the cell internalisation assay performed using compound 39 (fluorescein labelled Penetratin).

As discussed above, the 16 mer peptide subtending residues 43–58 of the *Antennapedia* homeodomain was originally identified as the minimal sequence retaining efficient translocation properties using peptides corresponding to residues 41–60, 43–58, 41–55, and 46–60. The results (FIG. 2) show that truncation at the C-terminus of peptide 1 results in a reduction in the degree of internalisation but nevertheless, the truncated peptides were still capable of translocating the cell membrane. Successive truncation from the N-terminus of peptide 1, however shows that significant levels of translocation are retained in the truncated peptides in many cases approaching the level attained by peptide 1 itself. Little activity was lost upon the first three truncations (11–13) but only about half of the original signal was left with derivatives 14 and 15. However, at the 10 mer to 7 mer (16–19) stage almost full membrane translocation efficiency relative to control peptide 1 was regained before a severe drop was observed with the C-terminal 6 mer peptide 20. This effect was reproducible in several independent experiments. While values for only one peptide concentration are shown in FIG. 2, dose-response curves for each individual peptide have shown that the same pattern was seen, regardless of peptide concentration. Non-specific binding in the absence of cells has been found to be uniform and negligible (results not shown).

1.43 Peptide Internalisation Assay of Fluorescein-labelled Penetratin 39

Figure 4:
FIG. 4 (A, B and C) show real-time visualisation of the cell internalisation assay performed using compound 39.

This assay permitted the study and measurement of cell internalisation without the possibility of observing artefacts emanating from the cell manipulations necessary with the biotinylated peptides. FIG. 4 shows the direct measurement of peptide internalisation into live cells. (squares when t=10 mins, diamonds when t=60 mins). As can be seen in FIG. 4, biotinylated Penetratin 1 localises predominantly to the cell nucleus and accumulates in the nucleoli, with lesser concentration in the cytosol. Clearly the distribution is very similar when the direct fluorescent probe 39 is used, thus validating the indirect biotin-avidin visualisation approach. The fact that Penetratin appears to localise mainly to the nucleus shows that this peptide can in fact translocate across both plasma and nuclear membranes. Nuceolar accumulation may be due to non-specific binding of the positively charged peptide to DNA.

Example 2

Further Truncated Penetratin Derivatives 2.1 In accordance with the methods described in sections 1.1 and 1.2 above, the following peptides were prepared;
RRMKWKK, (SEQ ID No. 2)
NRRMKWKK, (SEQ ID No. 6)
QNRRMKWKK, (SEQ ID No. 7)
KRMKWKK, (SEQ ID No. 9)
RKMKWKK, (SEQ ID No. 10)
RREKWKK, (SEQ ID No. 11)
RRQKWKK, (SEQ ID No. 12)
RROKWKK, (SEQ ID No. 4)
RRMKQKK, (SEQ ID No. 13)
RRMKWFK, (SEQ ID No. 14)
RORKWKK, (SEQ ID No. 15)
RRMWKKK, (SEQ ID No. 16)
RROWKKK, (SEQ ID No. 5)
RRMKKWK, (SEQ ID No. 17)
RROKKWK, (SEQ ID No. 18)
KKWKORR. (SEQ ID No. 36)
Each of these peptides were used in the peptide internalisation assay described in section 1.3 above a and was found to be internalised into cells.

Example 3

Preparation of a Series of Full-length Peptides in which each Residue in Turn was Substituted with Alanine (21–36)

3:1: Simultaneous Multiple Synthesis of Peptides 21–36
Peptides were prepared in the manner described in sections 1.1 and 1.2 above. Yield and analytical data for the title compounds are summarised in Table 3.

3.2 Peptide Internalisation Assays were Performed in Accordance with Section 1.3.

3.3: Results 3.3.1: Peptide Synthesis

Peptides 21–36 were prepared simultaneously using the so-called Multipin™ method (Valerio, R. M. et al., (1993) International Journal of Peptide and Protein Research 42,

| N° | Peptide | |
|---|---|---|
| 1 | Biotinyl-βAla-Arg-Gln-Ile-Lys-Ile-Trp-Phe-Gln-Asn-Arg-Arg-Met-Lys-Trp-Lys-Lys-NH$_2$ | (Seq ID. No. 19) |
| 21 | Biotinyl-βAla-Ala-Gln-Ile-Lys-Ile-Trp-Phe-Gln-Asn-Arg-Arg-Met-Lys-Trp-Lys-Lys-NH$_2$ | (Seq ID. No. 20) |
| 22 | Biotinyl-βAla-Arg-Ala-Ile-Lys-Ile-Trp-Phe-Gln-Asn-Arg-Arg-Met-Lys-Trp-Lys-Lys-NH$_2$ | (Seq ID. No. 21) |
| 23 | Biotinyl-βAla-Arg-Gln-Ala-Lys-Ile-Trp-Phe-Gln-Asn-Arg-Arg-Met-Lys-Trp-Lys-Lys-NH$_2$ | (Seq ID. No. 22) |
| 24 | Biotinyl-βAla-Arg-Gln-Ile-Ala-Ile-Trp-Phe-Gln-Asn-Arg-Arg-Met-Lys-Trp-Lys-Lys-NH$_2$ | (Seq ID. No. 23) |
| 25 | Biotinyl-βAla-Arg-Gln-Ile-Lys-Ala-Trp-Phe-Gln-Asn-Arg-Arg-Met-Lys-Trp-Lys-Lys-NH$_2$ | (Seq ID. No. 24) |
| 26 | Biotinyl-βAla-Arg-Gln-Ile-Lys-Ile-Ala-Phe-Gln-Asn-Arg-Arg-Met-Lys-Trp-Lys-Lys-NH$_2$ | (Seq ID. No. 25) |
| 27 | Biotinyl-βAla-Arg-Gln-Ile-Lys-Ile-Trp-Ala-Gln-Asn-Arg-Arg-Met-Lys-Trp-Lys-Lys-NH$_2$ | (Seq ID. No. 26) |
| 28 | Biotinyl-βAla-Arg-Gln-Ile-Lys-Ile-Trp-Phe-Ala-Asn-Arg-Arg-Met-Lys-Trp-Lys-Lys-NH$_2$ | (Seq ID. No. 27) |
| 29 | Biotinyl-βAla-Arg-Gln-Ile-Lys-Ile-Trp-Phe-Gln-Ala-Arg-Arg-Met-Lys-Trp-Lys-Lys-NH$_2$ | (Seq ID. No. 28) |
| 30 | Biotinyl-βAla-Arg-Gln-Ile-Lys-Ile-Trp-Phe-Gln-Asn-Ala-Arg-Met-Lys-Trp-Lys-Lys-NH$_2$ | (Seq ID. No. 29) |
| 31 | Biotinyl-βAla-Arg-Gln-Ile-Lys-Ile-Trp-Phe-Gln-Asn-Arg-Ala-Met-Lys-Trp-Lys-Lys-NH$_2$ | (Seq ID. No. 30) |
| 32 | Biotinyl-βAla-Arg-Gln-Ile-Lys-Ile-Trp-Phe-Gln-Asn-Arg-Arg-Ala-Lys-Trp-Lys-Lys-NH$_2$ | (Seq ID. No. 31) |
| 33 | Biotinyl-βAla-Arg-Gln-Ile-Lys-Ile-Trp-Phe-Gln-Asn-Arg-Arg-Met-Ala-Trp-Lys-Lys-NH$_2$ | (Seq ID. No. 32) |
| 34 | Biotinyl-βAla-Arg-Gln-Ile-Lys-Ile-Trp-Phe-Gln-Asn-Arg-Arg-Met-Lys-Ala-Lys-Lys-NH$_2$ | (Seq ID. No. 33) |
| 35 | Biotinyl-βAla-Arg-Gln-Ile-Lys-Ile-Trp-Phe-Gln-Asn-Arg-Arg-Met-Lys-Trp-Ala-Lys-NH$_2$ | (Seq ID. No. 34) |
| 36 | Biotinyl-βAla-Arg-Gln-Ile-Lys-Ile-Trp-Phe-Gln-Asn-Arg-Arg-Met-Lys-Trp-Lys-Ala-NH$_2$ | (Seq ID. No. 35) |

TABLE 4

Chromatographic and mass spectrometric analysis of peptides 1 and 21–36

| | | | MS[a] | Yield | | | Anal. RP-HPLC | |
|---|---|---|---|---|---|---|---|---|
| N° | Formula | M$_r$ | [M + H]$^+$ | mg[b] | μmol | %[c] | t$_R$ (min)[d] | Purity (%)[e] |
| 1  | C$_{117}$H$_{188}$N$_{38}$O$_{22}$S$_2$ | 2543.12 | 2544.1 | 6.7 | 2.6 | 50 | 19.0 | 78 |
| 21 | C$_{114}$H$_{181}$N$_{35}$O$_{11}$S$_2$ | 2458.01 | 2459.0 | 5.7 | 2.3 | 44 | 16.8 | 66 |
| 22 | C$_{115}$H$_{185}$N$_{37}$O$_{21}$S$_2$ | 2486.00 | 2487.1 | 6.2 | 2.5 | 47 | 16.9 | 79 |
| 23 | C$_{114}$H$_{182}$N$_{38}$O$_{22}$S$_2$ | 2501.04 | 2502.0 | 5.8 | 2.3 | 44 | 12.9 | 80 |
| 24 | C$_{114}$H$_{181}$N$_{37}$O$_{22}$S$_2$ | 2486.00 | 2487.0 | 6.4 | 2.6 | 48 | 17.6 | 76 |
| 25 | C$_{114}$H$_{182}$N$_{38}$O$_{22}$S$_2$ | 2501.04 | 2502.0 | 6.8 | 2.7 | 51 | 15.7 | 80 |
| 26 | C$_{109}$H$_{183}$N$_{37}$O$_{22}$S$_2$ | 2427.99 | 2429.0 | 6.7 | 2.7 | 52 | 12.5 | 80 |
| 27 | C$_{111}$H$_{184}$N$_{38}$O$_{22}$S$_2$ | 2467.02 | 2468.0 | 6.1 | 2.5 | 47 | 12.8 | 78 |
| 28 | C$_{115}$H$_{185}$N$_{37}$O$_{21}$S$_2$ | 2486.07 | 2487.1 | 6.5 | 2.6 | 49 | 15.9 | 79 |
| 29 | C$_{116}$H$_{187}$N$_{37}$O$_{21}$S$_2$ | 2500.09 | 2501.1 | 5.7 | 2.3 | 43 | 16.2 | 75 |
| 30 | C$_{114}$H$_{181}$N$_{35}$O$_{22}$S$_2$ | 2458.01 | 2459.0 | 5.6 | 2.3 | 43 | 18.7 | 77 |
| 31 | C$_{114}$H$_{181}$N$_{35}$O$_{22}$S$_2$ | 2458.01 | 2459.0 | 7.5 | 3.1 | 58 | 16.8 | 77 |
| 32 | C$_{115}$H$_{184}$N$_{38}$O$_{22}$S$_2$ | 2483.00 | 2484.0 | 6.4 | 2.6 | 49 | 15.4 | 96 |
| 33 | C$_{114}$H$_{181}$N$_{37}$O$_{22}$S$_2$ | 2486.03 | 2487.0 | 6.8 | 2.7 | 52 | 16.6 | 79 |
| 34 | C$_{109}$H$_{183}$N$_{37}$O$_{22}$S$_2$ | 2427.99 | 2429.0 | 8.5 | 3.5 | 66 | 14.3 | 83 |
| 35 | C$_{114}$H$_{181}$N$_{37}$O$_{22}$S$_2$ | 2486.03 | 2487.0 | 9.0 | 3.6 | 68 | 16.5 | 78 |
| 36 | C$_{114}$H$_{181}$N$_{37}$O$_{22}$S$_2$ | 2486.03 | 2487.0 | 10.1 | 4.0 | 76 | 16.4 | 73 |

[a] By DE MALDI-TOF MS.
[b] After solid-phase extraction and vacuum centrifugation.
[c] Relative to 5.3 μmol loading of synthesis 'crowns'.
[d] Gradient 15–35% acetonitrile (peptides 21–36) in 0.1% aq TFA over 20 min.
[e] From chromatogram integration (λ = 214 nm).

1–9). On average 2 coupling/deprotection cycles were performed per day and the entire synthesis, including biotinylation, cleavage/deprotection, purification by solid phase extraction, and analysis, were completed within a fortnight. The isolated and purified yields of the peptides ranged from 43–76% and purities were 66–96% (Table 2). The main impurities observed (MS, data not shown) were Met(O)-containing peptides. Methionine sulfoxide formation appears to be a general problem attendant in the Multipin method, presumably due to oxidation during the extended air drying cycles after the acylation and deprotection steps. In principle it is possible to back-reduce Met(O) in peptides; e.g., on an analytical scale we were able to convert the Met(O)-containing impurity to 1 cleanly using $NH_4I/Me_2S$ in TFA (Nicolás, E et al., (1995) Tetrahedron 51, 57013) (results not shown).

3.3.2: Effect of Residue Substitutions

Figure 5:
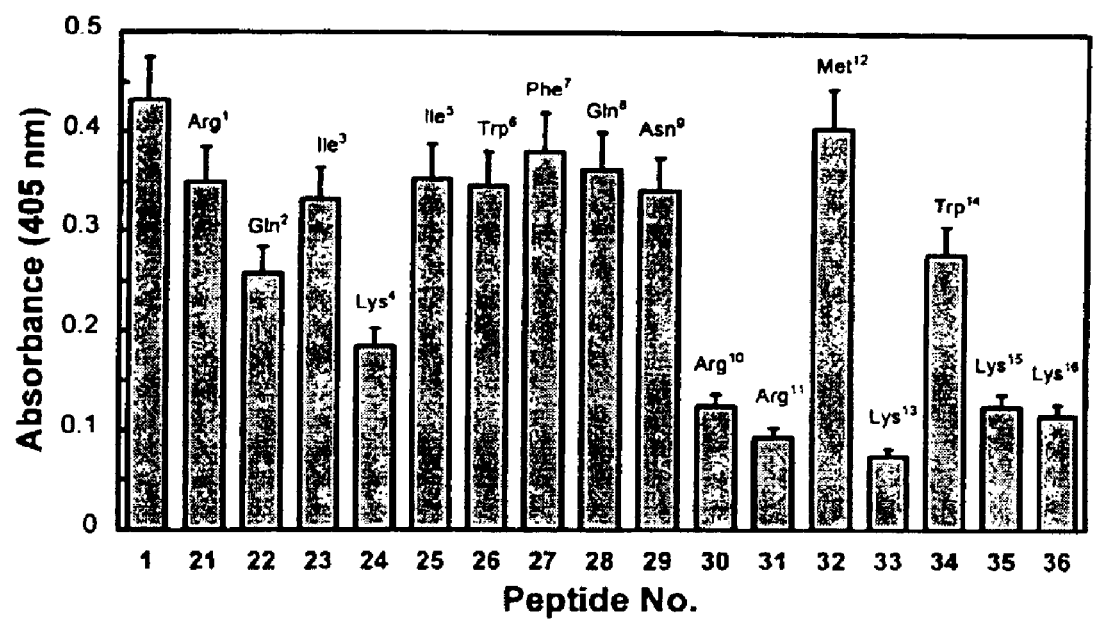
FIG. 5 shows the results of the cell internalisation assay performed using peptide carrier moieties prepared in accordance with the second aspect of the present invention.

The results using a set of peptides in which each residue in turn had been substituted with Ala (peptides 21–36) are shown in FIG. 5. The results clearly show that there are no very stringent requirements for any particular hydrophobic residue. It was shown elsewhere that e.g. both Ile residues can be substituted with Val, apparently without loss of activity (Brugidou, J et al., (1995) Biochemical and Biophysical Research Communications 214, 685–693). Furthermore, Met[12] is freely exchangeable with either Leu or Nle (results not shown). What these results clearly demonstrate is that in contrast to the prevelant opinion in the prior art, there is no necessity for the Trp[6].

Example 4

Further Modified Penetratin Derivatives

Using the method described in sections 1.1 and 1.2 above, further modified peptides of SEQ ID No. 1 may be prepared replacing the alanine residue shown in bold with any other amino acid residue, including the following paptides which were all active in the cell internalisation assay described in section 1.3 above;

| Modification to Penetratin* | Sequence | |
| --- | --- | --- |
| Met55 Nle | RQIKIWFQNRRROKWKK | (Seq ID No.56) |

-continued

| Modification to Penetratin* | Sequence | |
| --- | --- | --- |
| Met55 Nle (retro) | KKWKORRNQFWIKIQR | (Seq ID No.57) |
| Gln50Pro | RQIKIWFPNRRMKWKK | (Seq ID No.58) |
| 45,50,55Pro | RQPIKIWFPNRRMPWKK | (Seq ID No.59) |
| Trp48,56Phe | RQIKIFFQNRRMKFKK | (Seq ID No.60) |

Examples 5–17

Using the Methods Described Above Translocation Vectors Comprising the Carrier Moiety Linked to a Cargo were Prepared as Described

Example 5

H-Cys-βAla-Arg-Arg-Met-Lys-Trp-Lys-Lys-$NH_2$ (SEQ ID No. 61)

Starting from Rink Amide AM resin (0.69 mmol/g, Novabiochem), H-Cys(Trt)-βAla-Arg(Pmc)-Arg(Pmc)-Met-Lys(Boc)-Trp-Lys(Boc)-Lys(Boc)-resin (SEQ ID No. 61) was assembled. After deprotection (1.5 h), the crude peptide was obtained by precipitation from $Et_2O$, centrifugation/decantation, and drying. Aliquots (total 246 mg) were purified by preparative RP-HPLC (6.5–16.5% MeCN gradient) to afford the pure title compound (106.4 mg). Anal. RP-HPLC: $t_R$=15.8 min (6.5–16.5% MeCN gradient, purity>95% λ=214 nm). DE MALDI-TOF MS: $[M+H]^+$=1205.4 ($C_{52}H_{92}N_{20}O_9S_2$=1205.55).

2'-[Succinimidopropionoyl-(H-Cys-βAla-Arg-Arg-Met-Lys-Trp-Lys-Lys-$NH_2$)]paclitaxel (SEQ ID No. 61)

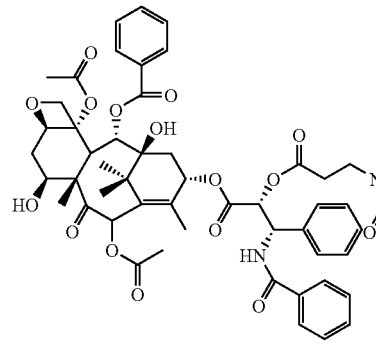
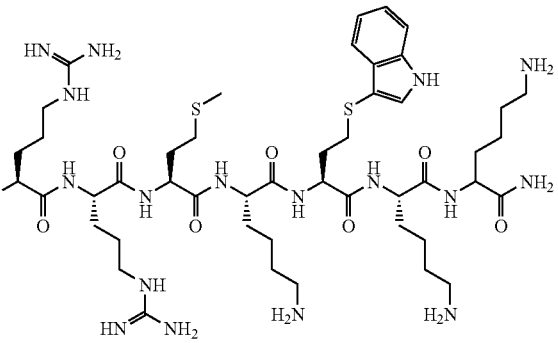

To a solution of 2'-(maleimidopropionoyl)paclitaxel (17 μmol, 17.4 mg) and H-Cys-βAla-Arg-Arg-Met-Lys-Trp-Lys-Lys-$NH_2$ (SEQ ID No. 61) (15 μmol, 18.1 mg) in DMF (1 mL) was added $Et_3N$ (2.0 μL). The mixture was stirred for 1 h, filtered and purified by preparative RP-HPLC (10–70% MeCN gradient). The pure title compound (9.4 mg) was obtained as a colourless solid. Anal. RP-HPLC: $t_R$=17.2 min (0–60% MeCN gradient, purity>97%). DE MALDI-TOF MS: $[M+H]^+$=2211.7 ($C_{106}H_{148}N_{22}O_{26}S_2$=2210.57.

Example 6

4-(Maleimidopropionoyl)podophyllotoxin

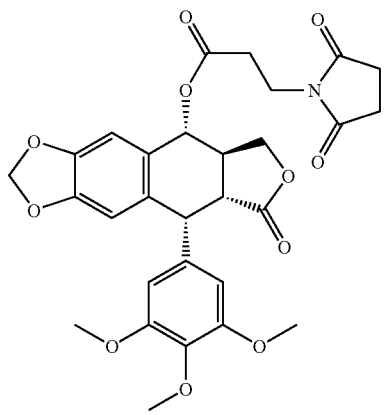

A solution of podophyllotoxin (60 μmol, 25.6 mg), 3-maleimidopropionic acid (0.31 mmol, 52.4 mg), DIC (0.17 mmol, 21.5 mg) and DMAP (80 μmol, 10 mg) in $CH_2Cl_2$ (2 mL) was stirred for 1 h. The solvent was evaporated in vacuo and the residue was redissolved in DMF/MeOH (1 mL) and purified by preparative RP-HPLC (20–70% MeCN gradient) to afford the pure title compound as a colourless solid (7.3 mg). Anal. RP-HPLC: $t_R$=20.1 min (0–60% MeCN gradient, purity>95%). $^1$H-NMR (300 MHz, $CDCl_3$) δ: 2.66–2.71 (t, J=6.3 Hz, 2H, $CH_2$), 2.82–2.84 (m, 2H, H2 and H3), 3.69 (s, 6H, $OCH_3$×2), 3.75 (s, 3H, $OCH_3$), 3.83 (t, J=6.3 Hz, 2H, $CH_2$), 4.12 (t, J=9.92 Hz, 1H, H11), 4.31 (m, 1H, H11), 4.53 (d, J=11.4 Hz, 1H, H1), 5.80 (d, J=8.7 Hz, 1H, H4), 5.92 (dd, J=5.49, 1.17 Hz, 2H, $OCH_2O$), 6.32 (s, 2H, H2'6') 6.47 (s, 1H, H8), 6.66 (s, 2H, CH=CH), 6.74 (s, 1H, H5).

4-[Succinimidopropionoyl-(H-Cys-βAla-Arg-Arg-Met-Lys-Trp-Lys-Lys-$NH_2$)]podophyllotoxin (SEQ ID No. 61)

To a solution of 4-(maleimidopropionoyl) podophyllotoxin (17.7 μmol, 10 mg) and H-Cys-βAla-Arg-Arg-Met-Lys-Trp-Lys-Lys-NH2 (SEQ ID No. 61) (25 μmol, 30.4 mg) in DMF (1.5 mL) was added $Et_3N$ (3.5 μL). The mixture was stirred for 40 min, filtered and purified by preparative RP-HPLC (0–60% MeCN gradient). The pure title compound was obtained as a colourless solid (17.8 mg, 57%). Anal. RP-HPLC: $t_R$=14.8 min (0–60% MeCN gradient, purity>98%). DE MALDI-TOF MS: $[M+H]^+$= 1772.3 ($C_{81}H_{119}N_{21}O_{20}S_2$=1771.07).

Example 7

H-Cys-βAla-D-Arg-D-Arg-D-Met-D-Lys-D-Trp-D-Lys-D-Lys-$NH_2$ (SEQ ID No. 61)

Starting from Rink Amide AM resin (0.69 mmol/g, Novabiochem), H-Cys(Trt)-βAla-D-Arg(Pmc)-D-Arg(Pmc)-D-Met-D-Lys(Boc)-D-Trp-D-Lys(Boc)-D-Lys(Boc)-resin (SEQ ID No. 61) was assembled. After deprotection (1.5 h), the crude peptide was obtained by precipitation from $Et_2O$, centrifugation/decantation, and drying. Aliquots (total 237 mg) were purified by preparative RP-HPLC (8–18% MeCN gradient) to afford the pure title compound (66 mg). Anal. RP-HPLC: $t_R$=12.9 min (9–19% MeCN gradient, purity>99%, λ=214 nm). DE MALDI-TOF MS: $[M+H]^+$= 1207.2 ($C_{52}H_{92}N_{20}O_9S_2$=1205.55).

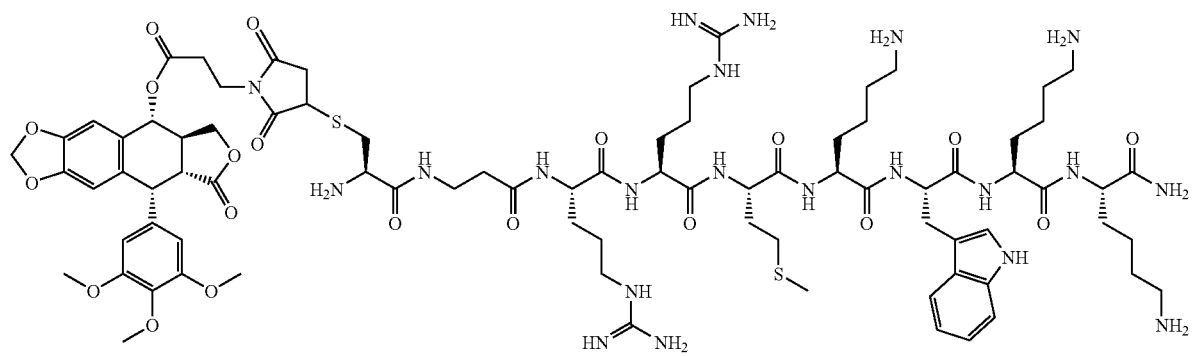

4-[Succinimidopropionoyl-(H-Cys-β-Ala-D-Arg-D-Arg-D-Met-D-Lys-D-Trp-D-Lys-D-Lys-NH₂)] podophyllotoxin (SEQ ID No. 61)

To a solution of 4-(maleimidopropionoyl) podophyllotoxin (18.9 μmol, 10.7 mg) and H-Cys-βAla-D-Arg-D-Arg-D-Met-D-Lys-D-Trp-D-Lys-D-Lys-NH₂ (SEQ ID No. 61) (28 μmol, 33.8 mg) in DMF (1.5 mL) was added Et₃N (1.5 μL). The mixture was stirred for 40 min, filtered and purified by preparative RP-HPLC (0–60% MeCN gradient). The pure title compound was obtained as a colourless solid (6.9 mg, 21%). Anal. RP-HPLC: $t_R$=14.8 min (0–60% MeCN gradient, purity>98%). DE MALDI-TOF MS: [M+H]⁺=1771.5 ($C_{81}H_{119}N_{21}O_{20}S_2$=1771.07).

Example 8

4'-(Maleimidopropionoyl)epipodophyllotoxin

A solution of 4'-demethylepipodophyllotoxin (12 mmol, 5 mg), 3-maleimidopropionic acid (50 μmol, 12.2 mg) and DIC (28 μmol, 3.47 mg) in pyridine (1 mL) was stirred for 30 min. MeOH (0.5 mL) was added and the mixture was purified by preparative RP-HPLC (0–60% MeCN gradient) to afford the pure title compound as a colourless solid (4.2 mg, 62%). Anal. RP-HPLC: $t_R$=17.6 min (0–60% MeCN gradient, purity>95%). ¹H-NMR (300 MHz, CDCl₃) δ: 2.84 (m, 1H, H3), 2.99 (t, J=7.44 Hz, 2H, CH₂-Mim), 3.32 (dd, J=14.04, 5.07 Hz, 1H, H2), 3.69 (s, 6H, OCH₃×2), 3.95 (t, J=7.44 Hz, 2H, CH₂-Mim), 4.39 (dd, J=8.13, 4.28 Hz, 2H, H11), 4.66 (d, J=5.00 Hz, 1H, H1), 4.89 (d, J=3.32 Hz, 1H, H4), 6.01 (d, J=6.42 Hz, 2H, OCH₂O), 6.32 (s, 2H, H2'6'), 6.57 (s, 1H, H8), 6.74 (s, 2H, CH=CH), 6.90 (s, 1H, H5). ¹³C-NMR (75 MHz, CDCl₃) δ: 28.64, 31.02, 32.55, 37.33, 39.53, 42.99, 55.15, 65.78, 66.56, 100.65, 106.54, 107.97, 109.65, 130.68, 130.92, 133.21, 136.96, 146.62, 147.61, 150.39, 167.36, 169.30, 173.89.

4'-[Succinimidopropionoyl-(H-Cys-βAla-Arg-Arg-Met-Lys-Trp-Lys-Lys-NH₂)]epipodophyllotoxin
(SEQ ID No. 61)

To a solution of 4'-(maleimidopropionoyl) epipodophyllotoxin (14 μmol, 7.9 mg) and H-Cys-βAla-Arg-Arg-Met-Lys-Trp-Lys-Lys-NH₂ (SEQ ID No. 61) (26 μmol, 31.5 mg) in DMF (1 mL) was added Et₃N (1.9 μL). After stirring for 40 min, the mixture was purified by preparative RP-HPLC (0–60% gradient) to afford the pure title compound as a colourless solid (15.8 mg, 63%). Anal. RP-HPLC: $t_R$=13.3 min (0–60% MeCN gradient, purity>98%). DE MALDI-TOF MS: [M+H]⁺=1757.2 ($C_{80}H_{117}N_{21}O_{20}S_2$=1757.05).

Example 9
4-(Iodoacetyl)podophyllotoxin

A mixture of podophyllotoxin (0.49 mmol, 204 mg), iodoacetic acid (1.03 mmol, 192 mg), DIC (0.552 mmol, 69.7 mg) and DMAP (0.164 mmol, 20 mg) in dry CH₂Cl₂ (5 mL) was cooled to 0° C. Pyridine (0.2 mL) was added and the reaction mixture was allowed to stir for 1 h at 0° C. The mixture was evaporated to dryness. The resulting light-yellow residue was redissolved in MeCN and was purified by preparative RP-HPLC (20–70% MeCN gradient) to afford the pure title compound as a colourless solid (89.5 mg). Anal. RP-HPLC: $t_R$=22.3 min (0–60% MeCN gradient, purity>95%). ¹H-NMR (300 MHz, CDCl₃) δ: 2.85 (m, 2H, H2,3), 3.70 (s, 6H, OCH₃×2), 3.72 (s, 2H, CH₂I), 3.74 (s, 3H, OCH₃), 4.13 (m, 1H, H11), 4.34 (m, 1H, H11), 4.53 (d, 1H, J=3.60 Hz, H1), 5.83 (d, 1H, J=8.43 Hz, H4), 5.93 (dd, 2H, J=4.35, 1.17 Hz, OCH₂O)), 6.31 (s, 2H, H2'6'), 6.48 (s, 1H, H8), 6.77 (s, 1H, H5).

4-[Acetyl-(H-Cys-βAla-Arg-Arg-Met-Lys-Trp-Lys-Lys-NH$_2$)]podophyllotoxin (SEQ ID No. 61)

A solution of 4-(iodoacetyl)podophyllotoxin (17 µmol, 10 mg) and H-Cys-βAla-Arg-Arg-Met-Lys-Trp-Lys-Lys-NH$_2$ (SEQ ID No. 61) (23 µmol, 28.6 mg) in DMF (1 mL) was added Et$_3$N (2.4 µL, 17 µmol). After stirring for 1 h MeCN (0.5 mL) was added and the mixture was purified by preparative RP-HPLC (0–60% MeCN gradient) to afford the pure title compound as a colourless solid (29.4 mg, 100%). Anal. RP-HPLC: t$_R$=14.1 min (0–60% MeCN gradient, purity>98%). DE MALDI-TOF MS: [M+H]$^+$=1661.0 (C$_{76}$H$_{114}$N$_{20}$O$_{18}$S$_2$=1659.97).

Example 10

4'-Demethyl-4-(iodoacetyl)epipodophyllotoxin

To a solution of 4'-demethylepipodophyllotoxin (0.26 mmol, 104 mg), iodoacetic acid (0.53 mmol, 98.8 mg), and DIC (0.32 mmol, 40.1 mg) in CH$_2$Cl$_2$ (2 mL) at 0° C. was added pyridine (50 µL) and DMAP (0.1 mmol, 12.8 mg). After 1 h stirring the solvents were evaporated. The residue was redissolved in DMF (1 mL) and purified by preparative RP-HPLC (20–60% MeCN gradient) to afford the pure title compound as a colourless solid (35.7 mg, 24%). Anal. RP-HPLC: t$_R$=20.3 min (0–60% MeCN gradient, purity>96%). $^1$H-NMR (300 MHz, CDCl$_3$) δ: 3.02 (m, 1H, H3), 3.20 (m, 1H, H2), 3.71 (s, 6H, OCH$_3$×2), 3.63 (s, 2H, CH$_2$I), 3.74 (s, 3H, OCH$_3$), 4.05 (m, 1H, H11), 4.27 (m, 1H, H11), 4.60 (d, 1H, J=4.94 Hz, H1), 6.06 (d, 1H, J=3.41 Hz, H4), 5.92 (m, 2H, OCH$_2$O), 6.21 (s, 2H, H2'6'), 6.49 (s, 1H, H8), 6.80 (s, 1H, H5).

4'-Demethyl-4-[acetyl-(H-Cys-βAla-Arg-Arg-Met-Lys-Trp-Lys-Lys-NH₂)]epipodophyllotoxin (SEQ ID No. 61)

To a solution of 4'-demethyl-4-(iodoacetyl) epipodophyllotoxin (17.6 μmol, 10 mg) and H-Cys-βAla-Arg-Arg-Met-Lys-Trp-Lys-Lys-NH₂ (SEQ ID No. 61) (14.9 μmol, 18 mg) in DMF (1 mL) was added Et₃N (2.1 μL, 15 μmol). After stirring for 1 h the reaction mixture was purified by preparative RP-HPLC (0–60% MeCN gradient) to afford the pure title compound as a colourless solid (11.2 mg, 46%). Anal. RP-HPLC: $t_R$=12.8 min (0–60% MeCN gradient, purity>98%). DE MALDI-TOF MS: [M+H]⁺= 1647.2 ($C_{75}H_{112}N_{20}O_{18}S_2$=1645.95).

Example 11

4-(Boc-Gly)podophyllotoxin

A mixture of podophyllotoxin (400 mg, 0.97 mmol), Boc-Gly-OH (510 mg, 2.91 mmol) DIC (1.73 mmol, 273 μL), DMAP (0.41 mmol, 50 mg) and pyridine (173 μL) in CH₂Cl₂ (5 mL) was stirred at for 1 h. The solvents were evaporated. The residue was redissolved in DMF (1.5 mL) and purified by RP-HPLC (20–70% MeCN gradient) to afford the pure title compound as a colourless solid (502.6 mg, 91%). Anal. RP-HPLC: $t_R$=22.1 min (0–60% MeCN gradient, purity>97%).

4-(H-Gly)podophyllotoxin

To a solution of 4-(Boc-Gly)podophyllotoxin (0.24 mmol, 137 mg) in CH₂Cl₂ (8 mL) was added TFA (0.5 mL). After stirring for 1 h the solvents were evaporated. The resulting light-yellow solid residue was purified by preparative RP-HPLC (10–70% MeCN gradient) to afford the pure title compound as a colourless solid (41.7 mg, 37%). Anal. RP-HPLC: $t_R$=15.2 min (0–60% MeCN gradient, purity>97%).

4-(Maleimidopropionoyl-Gly)podophyllotoxin

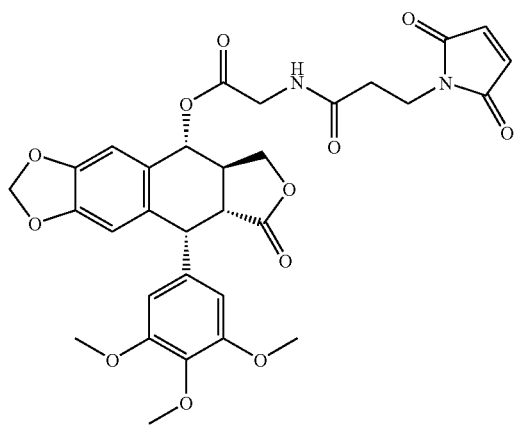

To a solution of 3-maleimidopropionic acid (70 μmol, 11.8 mg) and DIC (38 μmol, 4.83 mg) in DMF (1 mL) was added 4-(H-Gly)podophyllotoxin (17 μmol, 8 mg), DMAP (10 μmol, 1.2 mg) and pyridine (20 μL). After stirring for 1 h the mixture was purified by preparative RP-HPLC (0–60% MeCN gradient) to afford the pure title compound as a colourless solid (1.1 mg). Anal. RP-HPLC: $t_R$=18.2 min (0–60% MeCN gradient, purity>97%).

4-[(Succinimidopropionoyl-Gly)-(H-Cys-βAla-Arg-Arg-Met-Lys-Trp-Lys-Lys-NH$_2$)]podophyllotoxin (SEQ ID No. 61)

To a solution of 4-(maleimidopropionoyl-Gly) podophyllotoxin (18 μmol, 1.1 mg) and H-Cys-βAla-Arg-Arg-Met-Lys-Trp-Lys-Lys-NH$_2$ (SEQ ID No. 61) (4 μmol, 5 mg) in DMF (1 mL) was added Et$_3$N (0.5 μL, 4 μmol). The mixture was stirred for 1 h. It was diluted with MeCN (0.5 mL) and purified by preparative RP-HPLC (0–60% MeCN gradient) to afford the title compound as a colourless solid (1.1 mg, 33%). Anal. RP-HPLC: $t_R$=14.7 min (0–60% MeCN gradient, purity>97%). DE MALDI-TOF MS: $[M+H]^+$=1829.8 ($C_{83}H_{122}N_{22}S_2$=1828.12).

Example 12

H-Cys-Arg-Arg-Met-Lys-Trp-Lys-Lys-Cys-NH$_2$ (SEQ ID No. 62)

Starting from Rink Amide AM resin (0.69 mmol/g, Novabiochem), H-Cys(Trt)-Arg(Pmc)-Arg(Pmc)-Met-Lys(Boc)-Trp-Lys(Boc)-Lys(Boc)-Cys(Trt)-resin (SEQ ID No. 62) was assembled. After deprotection (1.5 h), the crude peptide was obtained by precipitation from Et$_2$O, centrifugation/decantation, and drying. Aliquots (total 258 mg) were purified by preparative RP-HPLC (9–19% MeCN gradient) to afford the pure title compound (132.4 mg). Anal. RP-HPLC: $t_R$=20.3 min (8–18% MeCN gradient, purity>99%, λ=214 nm). DE MALDI-TOF MS: $[M+H]^+$=1238.6 ($C_{52}H_{92}N_{20}O_9S_3$=1237.63).

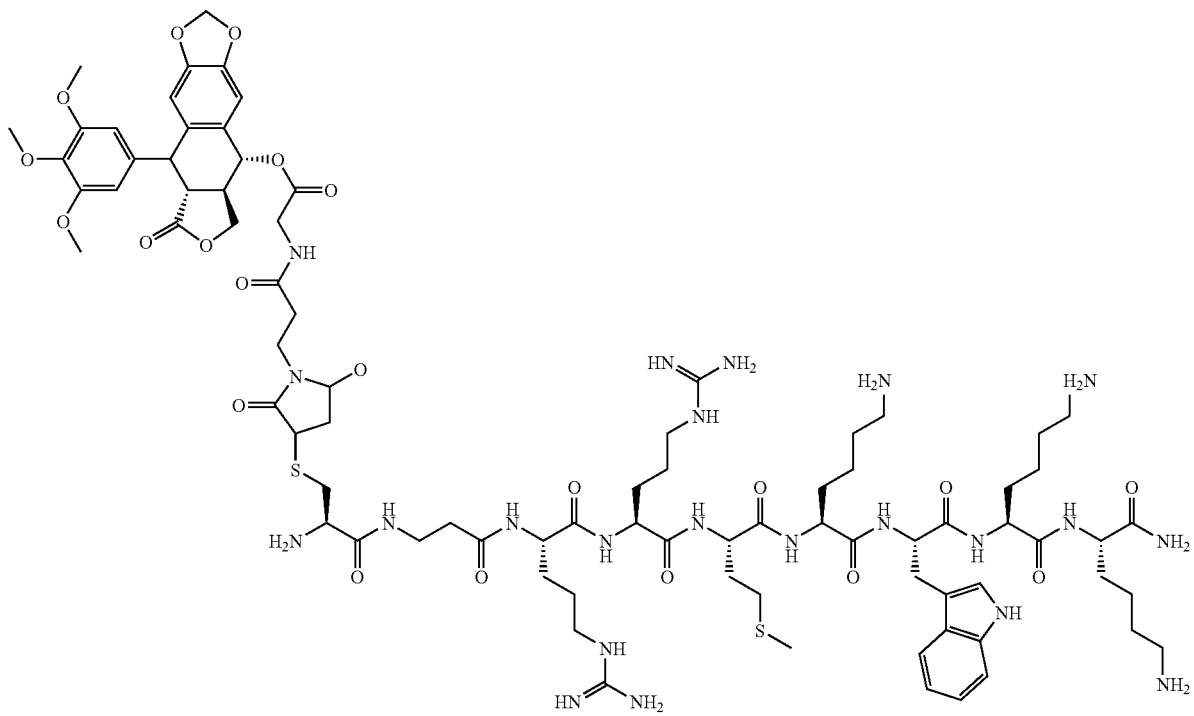

Bis-[4-(succinimidopropionoyl)podophyllotoxin]-
(H-Cys-Arg-Arg-Met-Lys-Trp-Lys-Lys-Cys-NH$_2$)
(SEQ ID No. 62)

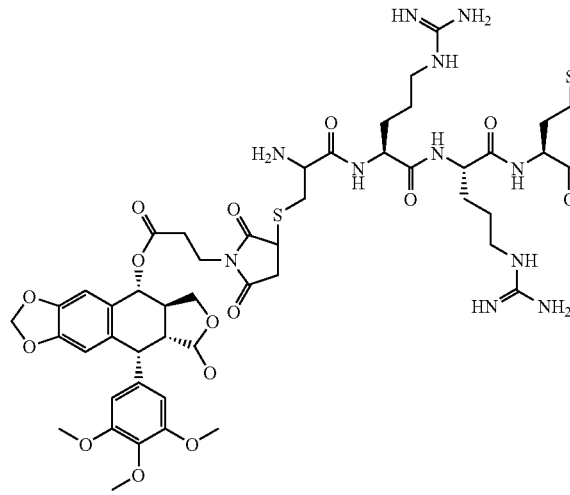
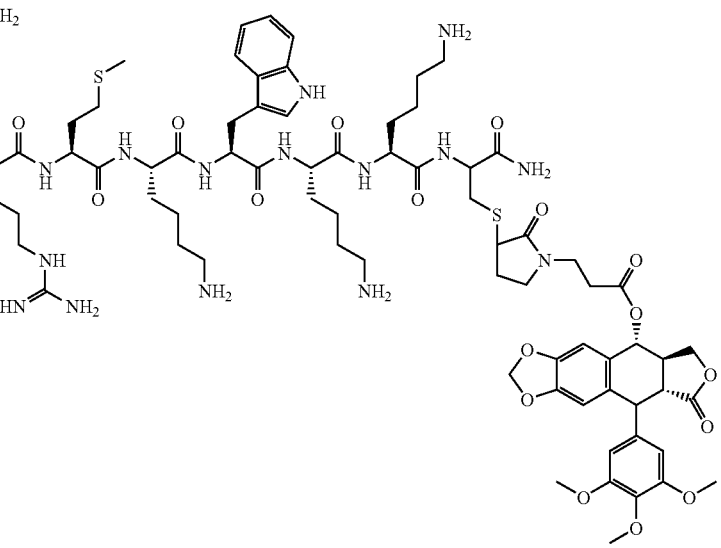

To a solution of 4-(maleimidopropionoyl)podophyllotoxin (19 μmol, 11 mg) and H-Cys-Arg-Arg-Met-Lys-Trp-Lys-Lys-Cys-NH$_2$ (SEQ ID No. 62) (12 μmol, 15 mg), in DMF (1 mL) was added Et$_3$N (2.8 μL). After stirring for 1 h the mixture was purified by preparative RP-HPLC (10–70% MeCN gradient) to afford the pure title compound as a colourless solid (9.0 mg, 32%). Anal. RP-HPLC: $t_R$=17.4 min (0–60% MeCN gradient, purity>98%). DE MALDI-TOF MS: [M+H]$^+$=2369.7 (C$_{110}$H$_{146}$N$_{22}$O$_{31}$S$_3$=2368.66).

Example 13

4'-(Succinimidopropionoyl)epipodophyllotoxin-(H-Cys-Arg-Arg-Met-Lys-Trp-Lys-Lys-Cys-NH$_2$)-10-O-(succinimidopropionoyl)camptothecin (SEQ ID No. 62)

To a solution of 10-O-(maleimidopropionoyl)camptothecin (0.005 mmol, 2.6 mg), 4'-(maleimidopropionoyl)epipodophyllotoxin (5.6 μmol, 3.1 mg), and H-Cys-Arg-Arg-Met-Lys-Trp-Lys-Lys-Cys-NH$_2$ (SEQ ID No. 62) (11 μmol, 13 mg), in DMF (1.5 mL) was added Et$_3$N (1.5 μL). After stirring for 1.5 h the mixture was purified by preparative RP-HPLC (10–70% MeCN gradient) to a afford the pure title compound as a colourless solid (1.9 mg). Anal. RP-HPLC: $t_R$=14.8 min (0–60% MeCN gradient, purity>96%). DE MALDI-TOF MS: [M+H]$^+$=2304.6 (C$_{107}$H$_{138}$N$_{24}$O$_2$S$_3$=2304.58).

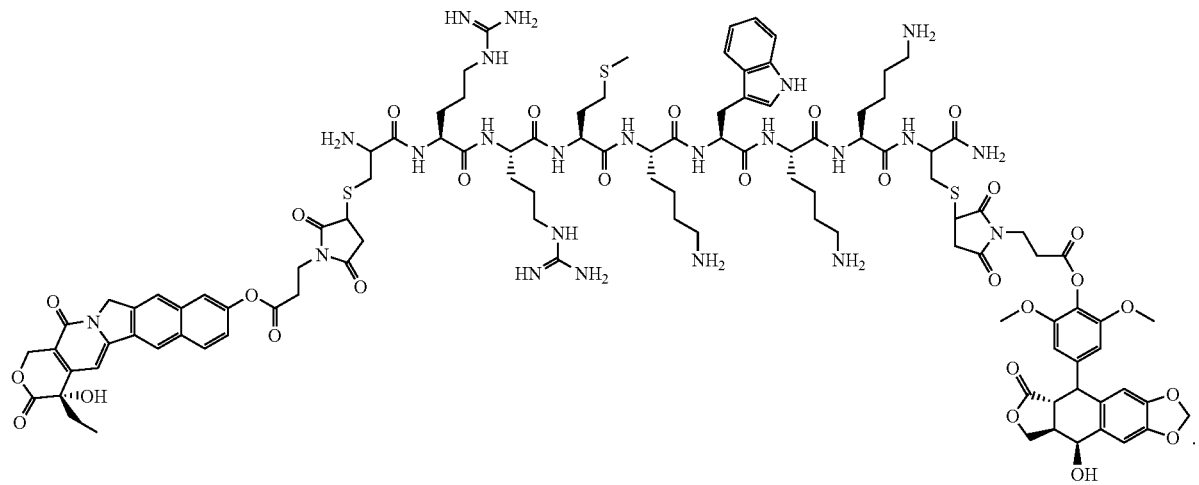

Example 14

4'-(Succinimidopropionoyl)epipodophyllotoxin-(H-Cys-Arg-Arg-Met-Lys-Trp-Lys-Lys-Cys-NH$_2$)-2'-(succinimidopropionyl)paclitaxel (SEQ ID No. 62)

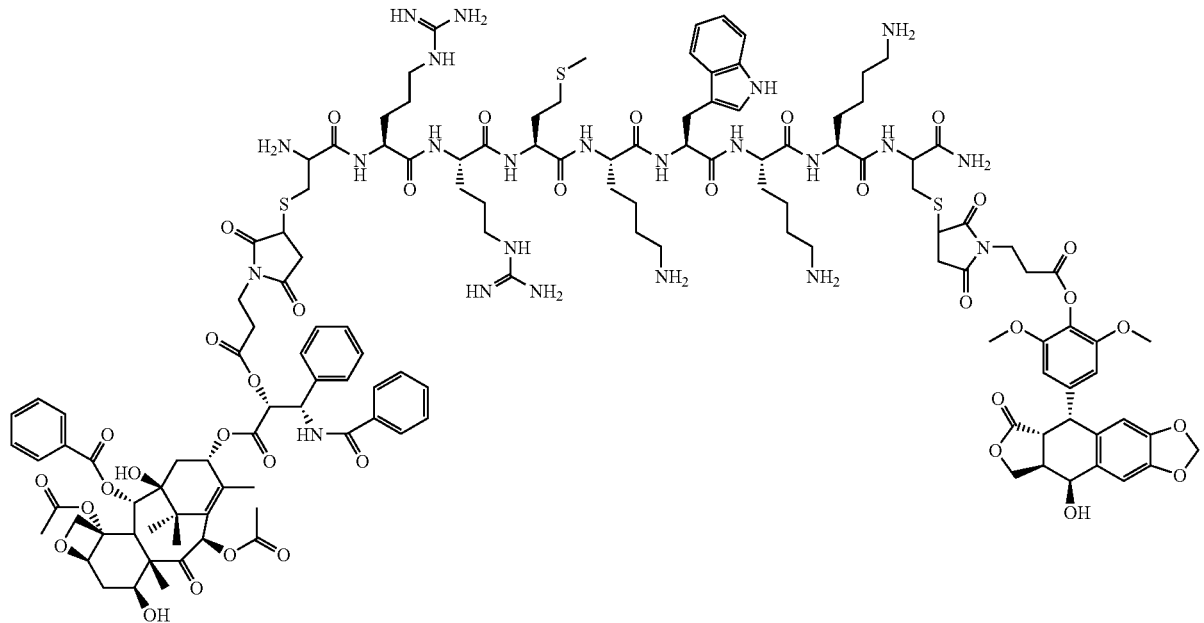

To a solution of 4'-[succinimidopropionoyl-(H-Cys-Arg-Arg-Met-Lys-Trp-Lys-Lys-Cys-NH$_2$)]epipodo-phyllotoxin (SEQ ID No. 62) (2 μmol, 3.5 mg), 2'-(maleimidopropionyl)paclitaxel (2 μmol, 2 mg) in DMF (1 mL) was added Et$_3$N (0.3 μL). After stirring for 1.5 h the reaction mixture was purified by preparative RP-HPLC (10–70% MeCN gradient) to afford the pure title compound as a colourless solid (1.5 mg). Anal. RP-HPLC: $t_R$=17.8 min (0–60% MeCN gradient, purity>98%). DE MALDI-TOF MS: [M+H]$^+$=2794.5 ($C_{134}H_{173}N_{23}O_{37}S_3$=2794.14).

Example 15

4'-Methoxy-4-[4''-aminoanilino-(succinimidopropionoyl)-(H-Cys-βAla-Arg-Arg-Met-Lys-Trp-Lys-Lys-NH$_2$)]epipodophyllotoxin (SEQ ID No. 61)

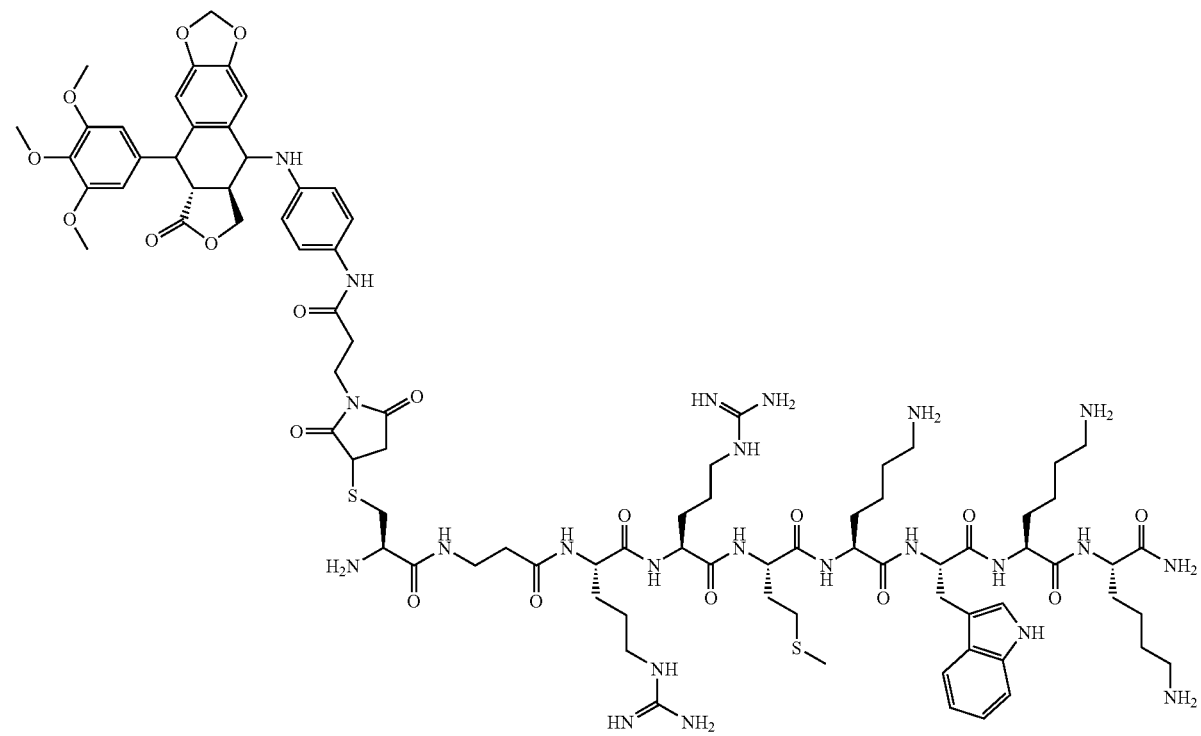

To a solution of 4'-methoxy-[4"-aminoanilino-(maleimidopropionoyl)]epipodophyllotoxin (7 µmol, 4.6 mg) and H-Cys-βAla-Arg-Arg-Met-Lys-Trp-Lys-Lys-NH$_2$ (SEQ ID No. 61) (14 µmol, 16.3 mg) in DMF (1 mL) was added Et$_3$N (1 µL). After stirring for 1 h, the mixture was purified by preparative RP-HPLC (0–60% MeCN gradient) to afford the pure title compound as a colourless solid (6.4 mg, 49%). Anal. RP-HPLC: $t_R$=15.2 min (0–60% MeCN gradient, purity>98%). DE MALDI-TOF MS: [M+H]$^+$= 1861.6 ($C_{87}H_{125}N_{23}O_9S_2$=1861.20).

Example 16

4'-Demethyl-4-[4"-aminoanilino-(maleimidopropionoyl)]epipodophyllotoxin

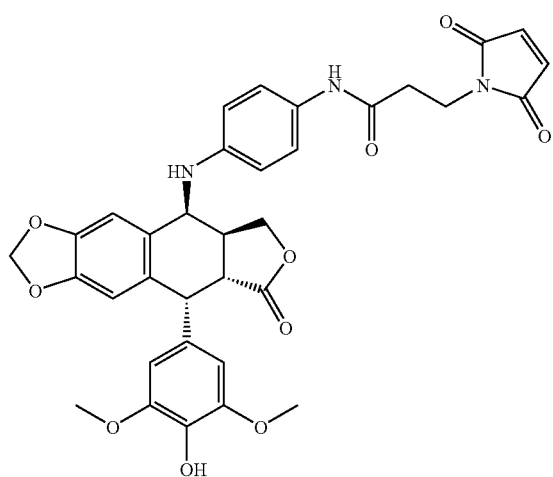

To a solution of 4'-demethyl-4-(4"-aminoanilino)epipodophyllotoxin (24 µmol, 12 mg), 3-maleimidopropionic acid (49 µmol, 8.3 mg), and DIC (27 µmol, 3.4 mg) in 1:1 DMF/CH$_2$Cl$_2$ (2 mL) was added pyridine (10 µL). After stirring for 1 h, the reaction mixture was evaporated. The resulting light-yellow solid was purified by preparative RP-HPLC (10–70% MeCN gradient) to afford the pure title compound as a colourless solid (5.3 mg, 34%). Anal. RP-HPLC: $t_R$=19.5 min (0–60% MeCN gradient, purity>96%). $^1$H-NMR (300 MHz, CDCl$_3$) δ: 2.65 (t, 2H, J=7.3 Hz, CH$_2$), 2.98 (m, 1H, H3), 3.17 (m, 1H, H2), 3.79 (s, 6H, OCH$_3$), 3.93 (t, 2H, J=7.0 Hz, CH$_2$), 3.99 (m, 1H, H5, H11), 4.38 (m, 1H, H11), 4.58 (d, 1H, J=4.95 Hz, H1), 4.64 (d, 1H, J=3.95 Hz, H4) 5.96 (m, 2H, OCH$_2$O), 6.33 (s, 2H, H2'6'), 6.49–6.53 (m, 3H, H8, Ar), 6.74 (s, 2H, CH═CH), 6.75 (s, 1H, H5), 7.33 (m, 2H, Ar).

4'-Demethyl-4-[4"-aminoanilino-(succinimidopropionoyl)-(H-Cys-βAla-Arg-Arg-Met-Lys-Trp-Lys-Lys-NH$_2$)]epipodophyllotoxin (SEQ ID No. 61)

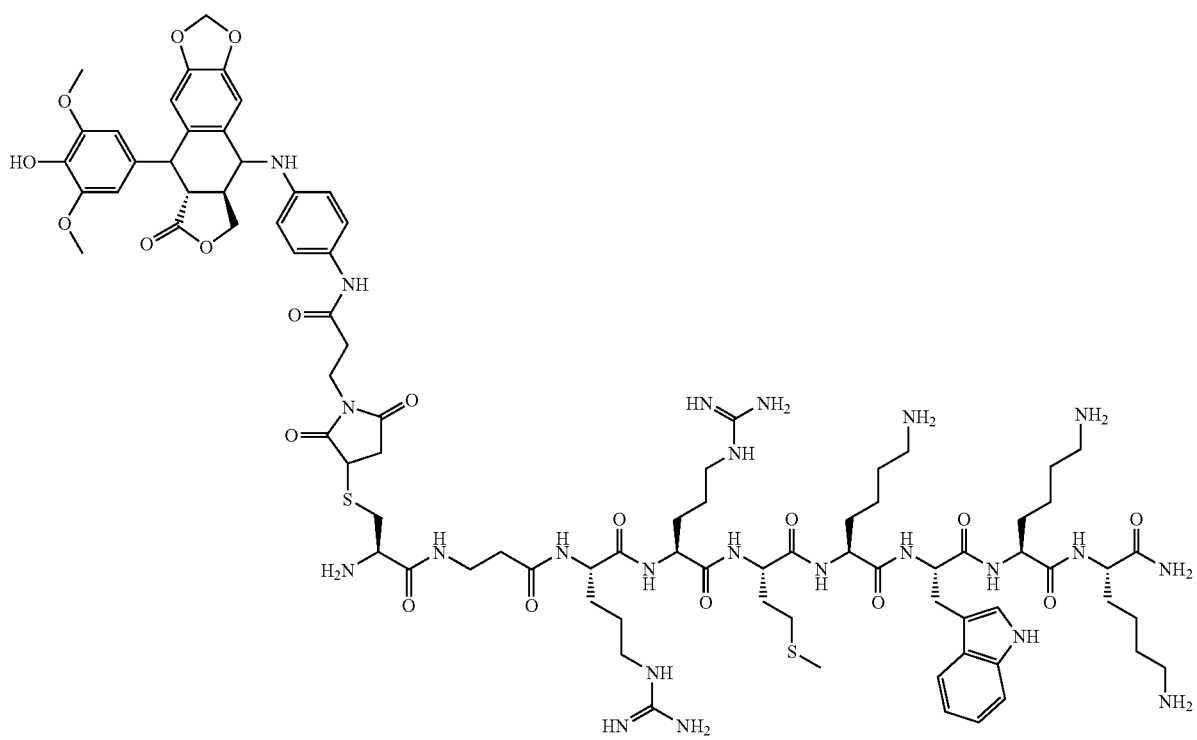

To a solution of 4'-demethyl-[4''-aminoanilino-(maleimidopropionoyl)]-epipodophyllotoxin (8.3 μmol, 5.3 mg) and H-Cys-βAla-Arg-Arg-Met-Lys-Trp-Lys-Lys-NH2 (SEQ ID No. 61) (13 μmol, 15.6 mg) in DMF (1.5 mL) was added Et$_3$N (2 μL). After stirring for 1 h, the mixture was purified by preparative RP-HPLC (0–60% MeCN gradient) to afford the pure title compound as a colourless solid (14.9 mg, 97%). Anal. RP-HPLC: $t_R$=13.7 min (0–60% MeCN gradient, purity>98%). DE MALDI-TOF MS: [M+H]$^+$= 1847.1 ($C_{86}H_{123}N_{23}O_{19}S_2$=1847.17).

Example 17

Evaluation of Etoposide and Podophyllotoxin Derivatives in Topoisomerase II Inhibition Assay Topoisomerase II assay—Plasmid DNA (0.3 μg) was incubated at 37° C. with 4 units of purified recombinant human topoisomerase II in cleavage buffer (30 mM Tris.HCl, pH 7.6, 60 mM NaCl, 3 mM ATP, 15 mM mercaptoethanol, 8 mM MgCl$_2$) with or without the addition of test compound (at 1 mM, 100 μM, or 10 μM final concentration). Reactions were stopped by the immediate addition of SDS (1% w/v final). Samples were treated with proteinase K (30 min at 37° C.) and extracted twice with an equal volume of 42:1 CHCl$_3$/i-amyl alcohol. After adding loading dye, samples were loaded to a 4×TAE, 1% agarose gel containing 0.5 mg/mL ethidium bromide and electrophoresed for 16–24 h. Topoisomerase II inhibition was judged by the production of linear plasmid DNA, representing trapped cleavage intermediate, and by the ratio of substrate (supercoiled DNA) to product (relaxed DNA). A relaxation assay was performed identically, except that the reaction buffer was optimised for the detection of catalysis rather than cleavage, i.e. only 2 units of enzyme were used per sample. The reaction buffer was 50 mM Tris.HCl, pH 8, 120 mM KCl, 0.5 mM ATP, 0.5 mM dithiothreitol, 10 mM MgCl$_2$. Topoisomerase II inhibition was judged by the ratio of substrate (supercoiled DNA) to product (relaxed DNA).

| Test Compound | Activity observed[a] |
|---|---|
| Etoposide | IC |
| Podophyllotoxin | — |
| 4'-Demethylepipodophyllotoxin | IC |
| 4'-Demethyl-4-(4''-aminoanilino)epipodophyllotoxin | I |
| H-βAla-Arg-Arg-Met-Lys-Trp-Lys-Lys-NH$_2$(Seq ID No.54) | — |
| 4-[Succinimidopropionoyl-(H-Cys-βAla-Arg-Arg-Met-Lys-Trp-Lys-Lys-NH$_2$)]podophyllotoxin (Seq ID No. 61) | — |
| 4-[Succinimidopropionoyl-(H-Cys-βAla-Arg-Arg-Met-Lys-Trp-Lys-Lys-NH$_2$)]epipodophyllotoxin (Seq.ID No. 61) | IC |
| 4'-Demethyl-4-[acetyl-(H-Cys-βAla-Arg-Arg-Met-Lys-Trp-Lys-Lys-NH$_2$)]epipodophyllotoxin (Seq ID No. 61) | IC |
| 4'-Demethyl-4-[4''aminoanilino-(succinimidopropionoyl)-(H-Cys-bAla-Arg-Arg-Met-Lys-Trp-Lys-Lys-NH$_2$)]epipodophyllotoxin (Seq ID No.61) | I |

Example 18

Comparison of Full Length and Truncated Penetratin as a Vector for a Drug Moiety In order to compare the cytotoxic biological effect on cancer cells (cell lines in Table 9) of the drug moieties applied using full length and truncated penatratin carrier moieties appropriate podophyllotoxin-conjugates (podophyllotoxin-(16 mer vector), 4-[succinimidopropionoyl-(H-Cys-Arg-Gln-Ile-Lys-Ile-Trp-Phe-Gln-Asn-Arg-Arg-Met-Lys-Trp-Lys-Lys-Gly-Cys-Gly-NH$_2$)]podophyllotoxin (SEQ ID No. 63); podophyllotoxin-7 mer vector, 4-[Succinimidopropionoyl-(H-Cys-βAla-Arg-Arg-Met-Lys-Trp-Lys-Lys-NH$_2$)]-podophyllotoxin) (SEQ ID No. 61), were exposed to cells at appropriate concentrations.

Serial dilutions of test compounds were applied to the cell lines. After incubation for 96 h, cytotoxicity was assessed using a standard sulforhodamine B (SRB) cell proliferation assay. IC$_{50}$ values are summarised in Table 9.

TABLE 9

| | A2780 | A2780 Cis$^R$ | CH1 | CH1 Dox$^R$ | CH1 Taxol$^R$ | HCT116 | HT29 | KM12 |
|---|---|---|---|---|---|---|---|---|
| podophyllotoxin, 16-mer[1] | 0.55 | 0.48 | 0.46 | 0.49 | 0.21 | 0.52 | 0.54 | 0.48 |
| podophyllotoxin, 7-mer[2] | 0.115 | 0.125 | 0.12 | 0.115 | 0.115 | 0.14 | 0.17 | 0.39 |

[1]maximum tolerated dose by iv administration ion mice is ca. 40 mg/kg (× mice)
[2]maximum tolerated dose by iv administration ion mice is ca. 75 mg/kg (× mice).

As can be seen from the Table, the truncated penetratin-podophyllotoxin conjugate is more effective in terms of anti-proliferative activity on tumour cells awhile exhibiting lower generalised toxicity.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A membrane translocation peptide carrier moiety consisting of the formula:

RQIKIWFQNRRMKWKK (SEQ ID NO. 1)
1                              16 wherein at least the terminal arginine amino acid residue is deleted from the amino terminus of said formula.

2. A carrier moiety according to claim 1, wherein up to 9 amino acid residues of said formula (SEQ ID No. 1) are deleted.

3. A carrier moiety according to claim 2, wherein from 6 to 9 amino acids residues of said formula (SEQ ID No. 1) are deleted.

4. A carrier moiety according to claim 3, wherein 9 amino acid residues of said formula (SEQ ID No. 1) are deleted.

5. A carrier moiety according to claim 3, consisting of the formula selected from the group consisting of RRMKWKK (SEQ ID No. 2), NRRMKWKK (SEQ ID No. 6), QNRRMKWKK (SEQ ID No. 7) and FQNRRMKWKK (SEQ ID No. 8).

6. A membrane translocation peptide carrier moiety consisting of the formula:

RQIKIWFQNRRMKWKK (SEQ ID NO: 1)
1                              16 wherein,
(a) 1 to 9 amino acid residues are deleted from the amino terminus of said formula (SEQ ID NO:1);
(b) 1 to 9 amino acid residues from the amino terminus of said formula (SEQ ID NO:1) are replaced by a naturally or non-naturally occurring amino acid residue, and the sixth amino acid residue of said formula (SEQ ID NO:1) is not tryptophan;
(c) one or two amino acid residues within the amino acid sequence RRMKWKK (SEQ ID NO:2) of said formula are replaced by a naturally or non-naturally occurring amino acid residue, and the sixth amino acid residue of said formula (SEQ ID NO:1) is not tryptophan;
(d) the order of two or more amino acid residues of said formula (SEQ ID NO:1) is reversed, and the sixth amino acid residue from either end of said peptide carrier moiety (SEQ ID NO:1) is not tryptophan;
(e) one or more amino acid residues of said formula (SEQ ID NO:1) are in peptoid form, and the sixth amino acid residue of said formula (SEQ ID NO:1) is not tryptophan;
(f) the (N—C—C) backbone of one or more amino acid residues of the peptide carrier moiety has been modified, and the sixth amino acid residue of said formula (SEQ ID NO:1) is not tryptophan;
(g) said peptide carrier moiety has (a) in combination with any of (b)–(f);
(h) said peptide carrier moiety has (b) in combination with any of (d)–(f);
(i) said peptide carrier moiety has (c) in combination with any of (d)–(f);
(j) said peptide carrier moiety has (d) in combination with any of (e)–(f); or
(k) said peptide carrier moiety has (e) in combination with (f).

7. A carrier moiety according to claim 6, consisting of the formula selected from the group consisting of: KRMKWKK (SEQ ID No. 9), RKMKWKK (SEQ ID No. 10), RREKWKK (SEQ ID No. 11), RRQKWKK (SEQ ID No. 12), RROKWKK (SEQ ID No. 4), RRMKQKK (SEQ ID No. 13), RRMKWFK (SEQ ID No. 14), RORKWKK (SEQ ID No. 15), RRMWKKK (SEQ ID No. 16), RROWKKK (SEQ ID No. 5), RRMKKWK (SEQ ID No. 18) and RROKKWK (SEQ ID No. 19).

8. A carrier moiety according to claim 1, consisting of the formula selected from the group consisting of QIKIWFQNRRMKWKK (SEQ ID No. 46), IKIWFQNRRMKWKK (SEQ ID No. 47), KIWFQNRRMKWKK (SEQ ID No. 48), IWFQNRRMKWKK (SEQ ID No. 49), WFQNRRMKWKK (SEQ ID No. 50), FQNRRMKWKK (SEQ ID NO. 51), QNRRMKWKK (SEQ ID No. 52), NRRMKWKK (SEQ ID No. 53), and RRMKWKK (SEQ ID No. 54).

9. A carrier moiety according to claim 6(b) or (c), wherein the naturally occurring amino acid residue is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

10. A membrane translocation peptide carrier moiety consisting of the formula selected from the group consisting of AQIKIWFQNRRMKWKK (SEQ ID No. 20), RAIKIWFQNRRMKWKK (SEQ ID No. 21), RQAKIWFQNRRMKWKK (SEQ ID No. 22); RQIAIWFQNRRMKWKK (SEQ ID No. 23), RQIKAWFQNRRMKWKK (SEQ ID No. 24), RQIKIAFQNRRMKWKK (SEQ ID No. 25), RQIKIWAQNRRMKWKK (SEQ ID No. 26), RQIKIWFANRRMKWKK (SEQ ID No. 27), RQIKIWFQARRMKWKK (SEQ ID No. 28), RQIKIWFQNARMKWKK (SEQ ID No. 29), RQIKIWFQNRAMKWKK (SEQ ID No. 30), RQIKIWFNQRRAKWKK (SEQ ID No. 31), RQIKIWFQNRRMAWKK (SEQ ID No. 32), RQIKIWFQNRRMKAKK (SEQ ID No. 33), RQIKIWFQNRRMKWAK (SEQ ID No. 34), and RQIKIWFQNRRMKWKA (SEQ ID No. 35).

11. A carrier moiety according to claim 1 or 6, wherein the free carboxyl group of the carboxy terminal amino acid residue is in the form —C(O)—NRR', wherein R and R' are each independently selected from the group consisting of: hydrogen, C1–6 alkyl, C1–6 alkylene or C1–6 alkynyl, aryl, each optionally substituted by a heteroatom.

12. A carrier moiety according to claim 11, wherein the free carboxyl group of the carboxy terminal amino acid residue is a carboxamide group.

13. A carrier moiety according to claim 12, consisting of the formula RRMKWKK-NH$_2$ (SEQ ID No. 2).

14. A carrier moiety according to claim 1 or 6, wherein one or more amino acid residues of said carrier moiety are in their L form.

15. A carrier moiety according to claim 1 or 6, wherein one or more amino acid residues of said carrier moiety are in their D form.

16. A carrier moiety according to claim 14, wherein the peptide carrier moiety is in the retro form.

17. A membrane translocation peptide carrier moiety of up to 15 amino acid residues and at least the formula:

RRMKWKK (I) (SEQ ID No. 2).

18. A membrane translocation peptide carrier moiety of up to 15 amino acid residues and at least the formula:

RRMKWKK (SEQ ID No. 2)

wherein,
(a) one or two amino acid residues of said formula (SEQ ID No.2) are replaced by a naturally occurring amino acid residue;
(b) one or two amino acid residues of said formula (SEQ ID No.2) are replaced by a non-naturally occurring amino acid residue;
(c) the order of two or more amino acid residues of said formula (SEQ ID No.2) is reversed;
(d) one or more amino acid residues of said peptide carrier moiety are in peptoid form;
(e) the (N—C—C) backbone of one or more amino acid residues of the peptide carrier moiety has been modified; or
(f) said peptide carrier moiety has any of (a) through (e) in combination.

19. A carrier moiety according to claim 18(a) or (b), wherein the naturally occurring amino acid residue is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

20. A carrier moiety according to claim 18(a) or (b), wherein the non-naturally occurring amino acid residue is selected from the group consisting of: Alpha and alpha-disubstituted amino acids, N-alkyl amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

21. A carrier moiety according to claim 6(b) or (c), wherein the non-naturally occurring amino acid residue is selected from the group consisting of: Alpha and alpha-disubstituted amino acids, N-alkyl amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

22. A carrier moiety according to claim 18, consisting of the formula selected from the group consisting of RQIKIWFQNRRMKWK (SEQ ID No. 37), RQIKIWFQNRRMKW (SEQ ID No. 38), RQIKIWFQNRRMK (SEQ ID No. 39), RQIKIWFQNRRM (SEQ ID NO. 40), RQIKIWFQNRR (SEQ ID NO. 41), RQIKIWFQNR (SEQ ID No. 42), RQIKIWFQN (SEQ ID No. 43), and RQIKIWFQ (SEQ ID No. 44) and ARQIKIWF (SEQ ID No. 45).

23. A carrier moiety according to claim 17 or 18, wherein the free carboxyl group of the carboxy terminal amino acid residue is in the form —C(O)—NRR', wherein R and R' are each independently selected from the group consisting of: hydrogen, C1–6 alkyl, C1–6 alkylene or C1–6 alkynyl, aryl, each optionally substituted by a heteroatom.

24. A carrier moiety according to claim 23, wherein the free carboxyl group of the carboxy terminal amino acid residue is a carboxamide group.

25. A carrier moiety according to claim 17 or 18, wherein one or more amino acid residues of said carrier moiety are in their L form.

26. A carrier moiety according to claim 17 or 18, wherein one or more amino acid residues of said carrier moiety are in their D form.

27. A carrier moiety according to claim 26, wherein the peptide carrier moiety is in the retro form.

28. A cell delivery vector precursor comprising a membrane translocation peptide carrier moiety and a linker moiety, said peptide carrier moiety comprising the formula:

RQIKIWFQNRRMKWKK (SEQ ID NO: 1)
1                                16 wherein,
(a) 1 to 9 amino acid residues are deleted from the amino terminus of said formula (SEQ ID NO:1);
(b) 1 to 9 amino acid residues from the amino terminus of said formula (SEQ ID NO:1) are replaced by a naturally or non-naturally occurring amino acid residue, and the sixth amino acid residue of said formula (SEQ ID NO:1) is not tryptophan;
(c) one or two amino acid residues within the amino acid sequence RRMKWKK (SEQ ID NO:2) of said formula are replaced by a naturally or non-naturally occurring amino acid residue, and the sixth amino acid residue of said formula (SEQ ID NO:1) is not tryptophan;
(d) the order of two or more amino acid residues of said formula (SEQ ID NO:1) is reversed, and the sixth amino acid residue from either end of said peptide carrier moiety (SEQ ID NO:1) is not tryptophan;
(e) one or more amino acid residues of said formula (SEQ ID NO:1) are in peptoid form, and the sixth amino acid residue of said formula (SEQ ID NO:1) is not tryptophan;
(f) the (N—C—C) backbone of one or more amino acid residues of the peptide carrier moiety has been modified, and the sixth amino acid residue of said formula (SEQ ID NO:1) is not tryptophan;
(g) said peptide carrier moiety has (a) in combination with any of (b)–(f);
(h) said peptide carrier moiety has (b) in combination with any of (d)–(f);
(i) said peptide carrier moiety has (c) in combination with any of (d)–(f);
(j) said peptide carrier moiety has (d) in combination with any of (e)–(f); or
(k) said peptide carrier moiety has (e) in combination with (f);
and wherein said cell delivery vector precursor does not comprise amino acid residues 1–16 of SEQ ID NO:1.

29. A cell delivery vector precursor according to claim 28, wherein the linker moiety is selected from the group consisting of bi- and multi-functional alkyl, aryl, aralkyl and peptidic moieties; alkyl, aryl and aralkyl aldehydes, acids, esters and anhydrides; sulphydryl and carboxyl groups; cyanuric bromide or chloride derivatives; carbonyldiimidazole, carbonyldiimidazole derivatives; succinimidyl esters; succinimidyl ester derivatives; sulphonic halides; and sulphonic halide derivatives.

30. A cell delivery vector precursor comprising a membrane translocation peptide carrier moiety and a targeting moiety, said peptide carrier moiety comprising the formula:

RQIKIWFQNRRMKWKK (SEQ ID NO: 1)
1                                16 wherein,
(a) 1 to 9 amino acid residues are deleted from the amino terminus of said formula (SEQ ID NO:1);
(b) 1 to 9 amino acid residues from the amino terminus of said formula (SEQ ID NO:1) are replaced by a naturally or non-naturally occurring amino acid residue, and the sixth amino acid residue of said formula (SEQ ID NO:1) is not tryptophan;
(c) one or two amino acid residues within the amino acid sequence RRMKWKK (SEQ ID NO:2) of said formula are replaced by a naturally or non-naturally occurring amino acid residue, and the sixth amino acid residue of said formula (SEQ ID NO:1) is not tryptophan;
(d) the order of two or more amino acid residues of said formula (SEQ ID NO:1) is reversed, and the sixth amino acid residue from either end of said peptide carrier moiety (SEQ ID NO:1) is not tryptophan;
(e) one or more amino acid residues of said formula (SEQ ID NO:1) are in peptoid form, and the sixth amino acid residue of said formula (SEQ ID NO:1) is not tryptophan;
(f) the (N—C—C) backbone of one or more amino acid residues of the peptide carrier moiety has been modified, and the sixth amino acid residue of said formula (SEQ ID NO:1) is not tryptophan;
(g) said peptide carrier moiety has (a) in combination with any of (b)–(f);
(h) said peptide carrier moiety has (b) in combination with any of (d)–(f);
(i) said peptide carrier moiety has (c) in combination with any of (d)–(f);
(j) said peptide carrier moiety has (d) in combination with any of (e)–(f); or
(k) said peptide carrier moiety has (e) in combination with (f);
and wherein said cell delivery vector precursor does not comprise amino acid residues 1–16 of SEQ ID NO:1.

31. A cell delivery vector precursor comprising a membrane translocation peptide carrier moiety, and a linker moiety, said peptide carrier moiety comprising up to 15 amino acid residues and at least the peptide of the formula:

RRMKWKK (SEQ ID No. 2)

wherein,
(a) one or two amino acid residues of said formula (SEQ ID No. 2) are replaced by a naturally occurring amino acid residue;
(b) one or two amino acid residues of said formula (SEQ ID No. 2) are replaced by a non-naturally occurring amino acid residue;
(c) the order of two or more amino acid residues of said formula (SEQ ID No. 2) is reversed;
(d) one or more amino acid residues of said peptide carrier moiety are in peptoid form;
(e) the (N—C—C) backbone of one or more amino acid residues of said peptide has been modified; or
(f) said peptide carrier moiety has any of (a) through (e) in combination, and wherein said cell delivery vector precursor does not comprise amino acid residues 1–16 of (SEQ ID No. 1).

32. A cell delivery vector precursor according to claim 31, wherein the linker moiety is selected from the group consisting of bi- and multi-functional alkyl, aryl, aralkyl and peptidic moieties; alkyl, aryl and aralkyl aldehydes, acids, esters and anhydrides; sulphydryl and carboxyl groups; cyanuric bromide or chloride derivatives; carbonyldiimidazole, carbonyldiimidazole derivatives; succinimidyl esters; succinimidyl ester derivatives; sulphonic halides; and sulphonic halide derivatives.

33. A cell delivery vector precursor comprising a membrane translocation peptide carrier moiety, a targeting moiety and a physiologically acceptable carrier, said peptide carrier moiety comprising up to 15 amino acid residues and at least the peptide of the formula:

RRMKWKK (SEQ ID No. 2), wherein
(a) one or two amino acid residues of said formula (SEQ ID No. 2) are replaced by a naturally occurring amino acid residue;
(b) one or two amino acid residues of said formula (SEQ ID No. 2) are replaced by a non-naturally occurring amino acid residue;
(c) the order of two or more amino acid residues of said formula (SEQ ID No. 2) is reversed;
(d) one or more amino acid residues of said peptide carrier moiety are in peptoid form;
(e) the (N—C—C) backbone of one or more amino acid residues of said peptide has been modified; or
(f) said peptide carrier moiety has any of (a) through (e) in combination, and wherein said cell delivery vector precursor does not comprise amino acid residues 1–16 of (SEQ ID No. 1).

34. A pharmaceutical composition comprising a membrane translocation peptide carrier moiety according to claim 1, 6, 17 or 18, and a physiologically acceptable carrier.

35. A pharmaceutical composition comprising a cell delivery vector precursor according to claim 28, 30, 31 or 33, and a physiologically acceptable carrier.

36. A cell delivery vector precursor according to claim 28 (b) or (c), wherein the naturally occurring amino acid residue of said carrier moiety is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

37. A cell delivery vector precursor according to claim 28 (b) or (c), wherein the non-naturally occurring amino acid residue of said carrier moiety is selected from the group consisting of: Alpha and alpha-disubstituted amino acids, N-alkyl amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

38. A cell delivery vector precursor according to claim 28, 30, 31 or 33, wherein the free carboxyl group of the carboxy terminal amino acid residue of said peptide carrier moiety is in the form —C(O)—NRR', wherein R and R' are each independently selected from the group consisting of: hydrogen, C1–6 alkyl, C1–6 alkylene or C1–6 alkynyl, aryl, each optionally substituted by a heteroatom.

39. A cell delivery vehicle according to claim 38, wherein free carboxyl group of the carboxy terminal amino acid residue of said peptide carrier moiety is a carboxamide group.

40. A cell delivery vector precursor according to claim 28, 30, 31 or 33, wherein one or more amino acid residues of said peptide carrier moiety are in their L form.

41. A cell delivery vector precursor according to claim 28, 30, 31 or 33, wherein one or more amino acid residues of said peptide carrier moiety are in their D form.

42. A cell delivery vector precursor according to claim 41, wherein the peptide carrier moiety is in the retro form.

43. A cell delivery vector precursor according to claim 30 or 33, wherein said cell delivery vector precursor further comprises a linker moiety.

44. A cell delivery vector precursor according to claim 43, wherein the linker moiety is selected from the group consisting of bi- and multi-functional alkyl, aryl, aralkyl and peptidic moieties; alkyl, aryl and aralkyl aldehydes, acids, esters and anhydrides; sulphydryl and carboxyl groups; cyanuric bromide or chloride derivatives; carbonyldiimidazole, carbonyldiimidazole derivatives; succinimidyl esters; succinimidyl ester derivatives; sulphonic halides; and sulphonic halide derivatives.

45. A cell delivery vector precursor according to claim 28 or 31, wherein said cell delivery vector precursor further comprises a targeting moiety.

46. A cell delivery vector precursor according to claim 30 (b) or (c), wherein the naturally occurring amino acid residue of said carrier moiety is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

47. A cell delivery vector precursor according to claim 30 (b) or (c), wherein the non-naturally occurring amino acid residue of said carrier moiety is selected from the group consisting of: Alpha and alpha-disubstituted amino acids, N-alkyl amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

48. A cell delivery vector precursor according to claim 30 (b) or (c), wherein the naturally occurring amino acid residue of said carrier moiety is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

49. A cell delivery vector precursor according to claim 30 (b) or (c), wherein the non-naturally occurring amino acid residue of said carrier moiety is selected from the group consisting of: Alpha and alpha-disubstituted amino acids, N-alkyl amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

50. A cell delivery vector precursor according to claim 31(a) or (b), wherein the naturally occurring amino acid residue of said carrier moiety is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

51. A cell delivery vector precursor according to claim 31(a) or (b), wherein the non-naturally occurring amino acid residue of said carrier moiety is selected from the group consisting of: Alpha and alpha-disubstituted amino acids, N-alkyl natural amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

52. A cell delivery vector precursor according to claim 33(a) or (b), wherein the naturally occurring amino acid residue of said carrier moiety is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

53. A cell delivery vector precursor according to claim 33(a) or (b), wherein the non-naturally occurring amino acid residue of said carrier moiety is selected from the group consisting of: Alpha and alpha-disubstituted amino acids, N-alkyl amino acids, lactic acid, halide derivatives of natural amino acids, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, L-thioproline, methyl derivatives of phenylalanine (Phe), L-Tyr (methyl), L-Phe (4-isopropyl), L-Tic (1,2,3,4-tetrahydroisoquinoline-3-carboxyl acid), L-diaminopropionic acid and L-Phe (4-benzyl).

54. A carrier moiety according to claim 11, wherein the heteroatom is selected from the group consisting of O, S and N.

55. A carrier moiety according to claim 23, wherein the heteroatom is selected from the group consisting of O, S and N.

56. A cell delivery vector precursor according to claim 38, wherein the heteroatom is selected from the group consisting of O, S, N.

57. A carrier moiety according to claim 20 or 21, wherein the halide derivative is selected from the group consisting of trifluorotyrosine, p-CL phenylalanine, p-Br phenylalanine, p-I-phenylalanine, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, and L-thioproline.

58. A cell delivery vector precursor according to claim 37, 49, 51 or 53, wherein the halide derivative is selected from the group consisting of trifluorotyrosine, p-CL phenylalanine, p-Br phenylalanine, p-I-phenylalanine, L-allyl-glycine, β-alanine, L-α-amino butyric acid, L-γ-amino butyric acid, L-α-amino isobutyric acid, L-ε-amino caproic acid, 7-amino heptanoic acid, L-methionine sulfone, L-norleucine, L-norvaline, p-nitro-L-phenylalanine, L-hydroxyproline, and L-thioproline.

59. A cell delivery vector precursor according to claim 29 or 32, wherein the linker is selected from the group consisting of maleimido benzoic acid, maleimido propionic acid and succinimido derivatives.

60. A cell delivery vector precursor according to claim 44, wherein the linker is selected from the group consisting of maleimido benzoic acid, maleimido propionic acid and succinimido derivatives.

61. The membrane translocation peptide carrier moiety of claim 6, wherein 1 to 9 amion acid residues are deleted from the amino terminus of said formula (SEQ ID No. 1).

62. The membrane translocation peptide carrier moiety of claim 6, wherein 1 to 9 amino acid residues from the amino terminus of said (SEQ ID No. 1) are replaced by a naturally or non-naturally occurring amino acid residues, and the sixth amino acid residue of said formula (SEQ ID No. 1) is not tryptophan.

63. The membrane translocation peptide carrier moiety of claim 6, wherein one or two amino acid residues within the amino acid sequence RRMKWKK (SEQ ID No. 2) of said formula are replaced by a naturally or non-naturally occurring amino acid residue, and the sixth amino acid residue of said formula (SEQ ID No. 1) is not tryptophan.

64. The membrane translocation peptide carrier moiety of claim 6, wherein the order of two or more amino acid residues of said formula (SEQ ID No. 1) is reversed, and the sixth amino acid residue from either end of said peptide carrier moiety (SEQ ID No. 1) is not tryptophan.

65. The membrane translocation peptide carrier moiety of claim 6, wherein one or more amino acid residues of said formula (SEQ ID NO. 1) are in peptoid form, and the sixth amino acid residue of said formula (SEQ ID No. 1) is not tryptophan.

66. The membrane translocation peptide carrier moiety of claim 6, wherein the (N-C-C) backbone of one or more amino acid residues of the peptide carrier moiety has been modified, and the sixth amino acid residue of said formula (SEQ ID NO. 1) is not tryptophan.

67. The membrane translocation peptide carrier moiety of claim 18, wherein one or two amino acid residues of said formula (SEQ ID No. 2) are replaced by a naturally occurring amino acid residue.

68. The membrane translocation peptide carrier moiety of claim 18, wherein one or two amino acid residues of said formula (SEQ ID No. 2) are replaced by a non-naturally occurring amino acid residue.

69. The membrane translocation peptide carrier moiety of claim 18, wherein (c) the order of two or more amino acid residues of said formula (SEQ ID No. 2) is reversed.

70. The membrane translocation peptide carrier moiety of claim 18, wherein one or more amino acid residues of said peptide carrier moiety are in peptoid form.

71. The membrane translocation peptide carrier moiety of claim 18, wherein the (N-C-C) backbone of one or more amino acid residues of the peptide carrier moiety has been modified.

72. The cell delivery vector precursor of claim 28, wherein 1 to 9 amino acid residues are deleted from the amino terminus of said formula (SEQ ID No. 1).

73. The cell delivery vector precursor of claim 28, wherein 1 to 9 amino acid residues from the amino terminus of said formula (SEQ ID No. 1) are replaced by a naturally or non-naturally occurring amino acid residue, and the sixth amino acid residue of said formula (SEQ ID No. 1) is not tryptophan.

74. The cell delivery vector precursor of claim 28, wherein one or two amino acid residues within the amino acid sequence RRMKWKK (SEQ ID No. 2) of said formula are replaced by a naturally or non-naturally occurring amino acid residue, and the sixth amino acid residue of said formula (SEQ ID No. 1) is not tryptophan.

75. The cell delivery vector precursor of claim 28, wherein the order of two or more amino acid residues of said formula (SEQ ID No. 1) is reversed, and the sixth amino acid residue from either end of said peptide carrier moiety (SEQ ID No. 1) is not tryptophan.

76. The cell delivery vector precursor of claim 28, wherein one or more amino acid residues of said formula (SEQ ID NO. 1) are in peptoid form, and the sixth amino acid residue of said formula (SEQ ID No. 1) is not tryptophan.

77. The cell delivery vector precursor of claim 28, wherein the (N- C-C) backbone of one or more amino acid residues of the peptide carrier moiety has been modified, and the sixth amino acid residue of said formula (SEQ ID NO. 1) is not tryptophan.

78. The cell delivery vector precursor of claim 30, wherein 1 to 9 amino acid acid residues are deleted from the amino terminus of said formula (SEQ ID No. 1).

79. The cell delivery vector precursor of claim 30, wherein 1 to 9 amino acid acid residues from the amino terminus of said formula (SEQ ID No. 1) are replaced by a naturally or non-naturally occurring amino acid residue, and the sixth amino acid residue of said formula (SEQ ID No. 1) is not tryptophan.

80. The cell delivery vector precursor of claim 30, wherein one or two amino acid residues within the ammo acid sequence RRMKWKK (SEQ ID No. 2) of said formula are replaced by a naturally or non-naturally occurring amino acid residue, and the sixth amino acid residue of said formula (SEQ ID No. 1) is not tryptophan.

81. The cell delivery vector precursor of claim 30, wherein the order of two or more amino acid residues of said formula (SEQ ID No. 1) is reversed, and the sixth amino acid residue from either end of said peptide carrier moiety (SEQ ID No. 1) is not tryptophan.

82. The cell delivery vector precursor of claim 30, wherein one or more amino acid residues of said formula (SEQ ID No. 1) are in peptoid form, and the sixth amino acid residue of said formula (SEQ ID No. 1) is not tryptophan.

83. The cell delivery vector precursor of claim 30, wherein the (N- C-C) backbone of one or more amino acid residues of the peptide carrier moiety has been modified, and the sixth amino acid residue of said formula (SEQ ID No. 1) is not tryptophan.

84. The cell delivery vector precursor of claim 31, wherein one or two amino acid residues of said formula (SEQ ID No. 2) are replaced by a naturally occurring amino acid residue.

85. The cell delivery vector precursor of claim 31, wherein one or two amino acid residues of said formula (SEQ ID No. 2) are replaced by a non- naturally occurring amino acid residue.

86. The cell delivery vector precursor of claim 31, wherein the order of two or more amino acid residues of said formula (SEQ ID No. 2) is reversed.

87. The cell delivery vector precursor of claim 31, wherein one or more amino acid residues of said peptide carrier moiety are in peptoid form.

88. The cell delivery vector precursor of claim 31, wherein the (N-C-C) backbone of one or more amino acid residues of said peptide has been modified.

89. The cell delivery vector precursor of claim 33, wherein one or two amino acid residues of said formula (SEQ ID No. 2) are replaced by a naturally occurring amino acid residue.

90. The cell delivery vector precursor of claim 33, wherein one or two amino acid residues of said formula (SEQ ID No. 2) are replaced by a non- naturally occurring amino acid residue.

91. The cell delivery vector precursor of claim 33 wherein the order of two or more amino acid residues of said formula (SEQ ID No. 2) is reversed.

92. The cell delivery vector precursor of claim 33, wherein one or more amino acid residues of said peptide carrier moiety are in peptoid form.

93. The cell delivery vector precursor of claim 33, wherein the (N- C-C) backbone of one or more amino acid residues of said peptide has been modified.

* * * * *